US012564678B2

(12) United States Patent
Zhong et al.

(10) Patent No.: US 12,564,678 B2
(45) Date of Patent: Mar. 3, 2026

(54) SYSTEMS AND METHODS FOR OPTIMIZING MEDICAMENT DOSING

(71) Applicant: Medtronic MiniMed, Inc., Northridge, CA (US)

(72) Inventors: Yuxiang Zhong, Arcadia, CA (US); Anirban Roy, Agoura Hills, CA (US); Pratik J. Agrawal, Porter Ranch, CA (US); Ali Dianaty, Porter Ranch, CA (US); Arthur Mikhno, Princeton, NJ (US); Shruti Rastogi, Northridge, CA (US); Taly G. Engel, Los Angeles, CA (US); Michael P. Stone, Long Beach, CA (US); Boyi Jiang, Pasadena, CA (US); Sinu Bessy Abraham, Gallatin, TN (US); Dae Y. Kang, Los Angeles, CA (US)

(73) Assignee: MEDTRONIC MINIMED, INC., Northridge (CA)

( * ) Notice: Subject to any disclaimer, the term of this patent is extended or adjusted under 35 U.S.C. 154(b) by 780 days.

(21) Appl. No.: 17/537,660

(22) Filed: Nov. 30, 2021

(65) Prior Publication Data

US 2022/0168506 A1 Jun. 2, 2022

Related U.S. Application Data

(60) Provisional application No. 63/119,720, filed on Dec. 1, 2020.

(51) Int. Cl.
*A61M 5/172* (2006.01)
*A61M 5/168* (2006.01)

(52) U.S. Cl.
CPC ...... *A61M 5/1723* (2013.01); *A61M 5/16877* (2013.01); *A61M 2205/3327* (2013.01);
(Continued)

(58) Field of Classification Search
CPC ...... A61M 2205/33; A61M 2205/3327; A61M 2205/50; A61M 2205/502;
(Continued)

(56) References Cited

U.S. PATENT DOCUMENTS 4,755,173 A 7/1988 Konopka et al.
5,391,250 A 2/1995 Cheney, II et al.
(Continued)

OTHER PUBLICATIONS

International Search Report and Written Opinion of the International Searching Authority issued in corresponding application PCT/US2021/061067 mailed Mar. 3, 2022 (14 pages).
(Continued)

*Primary Examiner* — Shefali D Patel
(74) *Attorney, Agent, or Firm* — Weaver Austin Villeneuve & Sampson LLP

(57) ABSTRACT

A system for monitoring a patient, wherein the system includes one or more processors and a sensor device implemented in circuitry. The system is configured to measure, using the sensor device, a blood glucose status of the patient, and determine, using the one or more processors, an initial insulin dose for the patient based on the blood glucose status of the patient. The system is further configured to optimize the initial insulin dose for the patient, based at least in part on a correction factor, to create an optimized insulin dose for the patient. The system is configured to facilitate therapy, using the one or more processors, based on the optimized insulin dose.

20 Claims, 16 Drawing Sheets

(52) U.S. Cl.
  CPC ... *A61M 2205/50* (2013.01); *A61M 2205/502*
        (2013.01); *A61M 2230/201* (2013.01); *A61M*
                                    *2230/63* (2013.01)

(58) Field of Classification Search
  CPC ...... A61M 2230/005; A61M 2230/201; A61M
        2230/63; A61M 5/16877; A61M 5/172;
                            A61M 5/1723; A61M 2205/52
  See application file for complete search history.

(56) References Cited

U.S. PATENT DOCUMENTS

| | | |
|---|---|---|
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Nunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Stoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 9,672,328 B2 | 6/2017 | Saint et al. |
| 10,835,727 B2 | 11/2020 | Montalvo et al. |
| 2007/0123819 A1 | 5/2007 | Mernoe et al. |
| 2010/0160861 A1 | 6/2010 | Causey, III et al. |
| 2019/0175841 A1 | 6/2019 | Sjolund et al. |
| 2020/0135319 A1 | 4/2020 | Vleugels |
| 2020/0294645 A1 | 9/2020 | Vleugels |
| 2020/0327973 A1 | 10/2020 | Pryor et al. |

OTHER PUBLICATIONS

EP Office Action dated Aug. 26, 2025 in EP Application No. 21831175.1.

FIG 1: BOLUS CALCULATOR

- Bolus Calculators may be based on the Blood Glucose values

- Potential to use CGM values for bolus calculators

- Potential to augment Bolus Wizard by considering glucose trend information

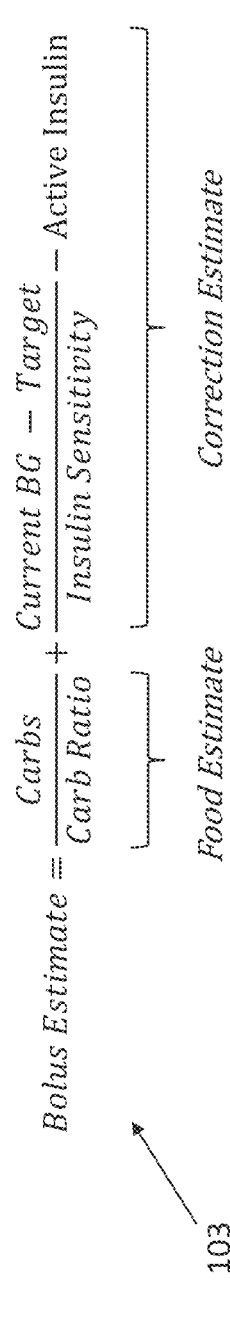

$$Bolus\ Estimate = \underbrace{\frac{Carbs}{Carb\ Ratio}}_{Food\ Estimate} + \underbrace{\frac{Current\ BG\ -\ Target}{Insulin\ Sensitivity}\ -\ Active\ Insulin}_{Correction\ Estimate}$$

103

Figure 2:
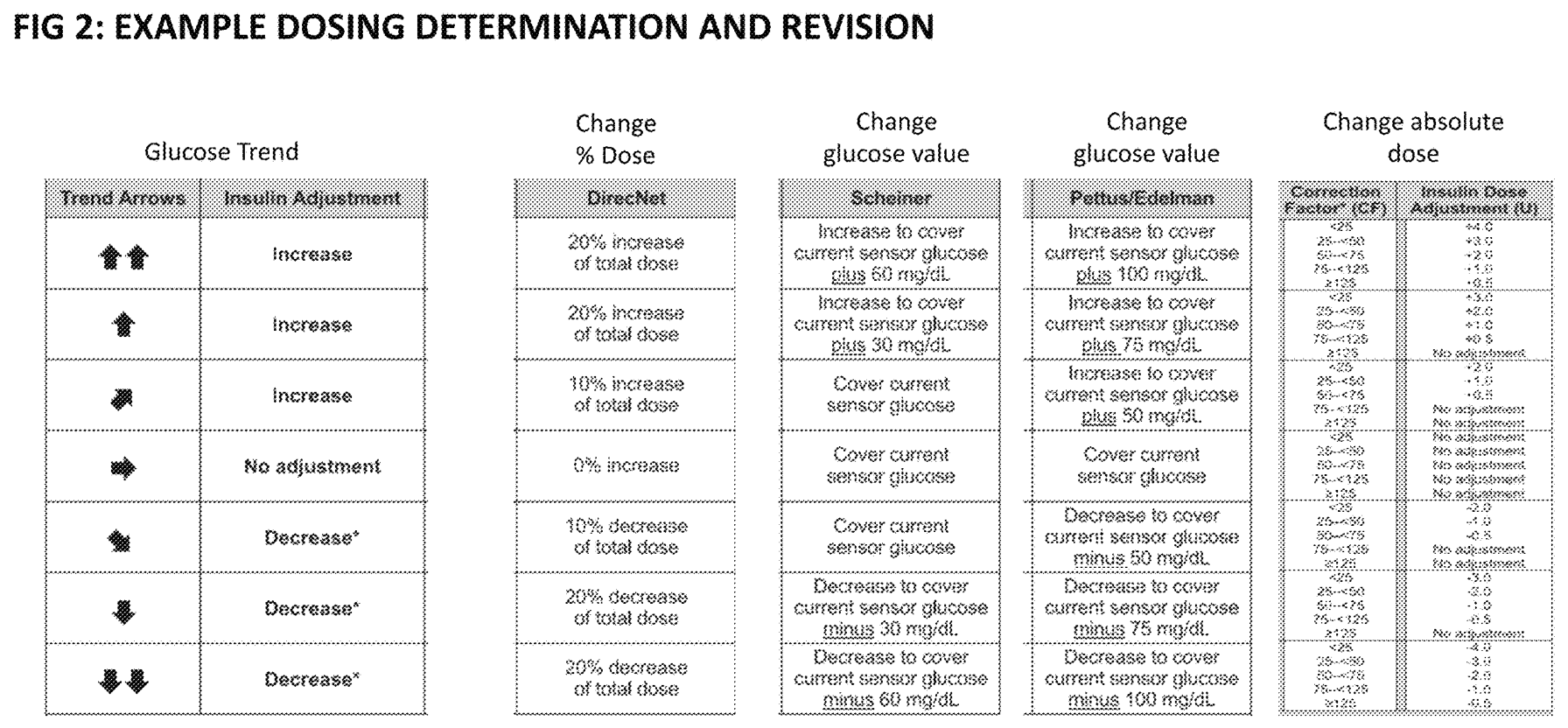

FIG 2: EXAMPLE DOSING DETERMINATION AND REVISION

| Glucose Trend | | Change % Dose | Change glucose value | Change glucose value | Change absolute dose | |
|---|---|---|---|---|---|---|
| Trend Arrows | Insulin Adjustment | DreaMed | Schreiner | Pettus/Edelman | Correction Factor (CF) | Insulin Dose Adjustment IU |
| ⬆⬆ | Increase | 20% increase of total dose | Increase to cover current sensor glucose plus 60 mg/dL | Increase to cover current sensor glucose plus 100 mg/dL | | |
| ⬆ | Increase | 20% increase of total dose | Increase to cover current sensor glucose plus 30 mg/dL | Increase to cover current sensor glucose plus 75 mg/dL | | |
| ⬆ | Increase | 10% increase of total dose | Cover current sensor glucose | Increase to cover current sensor glucose plus 50 mg/dL | | No adjustment |
| ⬆ | No adjustment | 0% increase | Cover current sensor glucose | Cover current sensor glucose | | No adjustment |
| ⬇ | Decrease* | 10% decrease of total dose | Cover current sensor glucose | Decrease to cover current sensor glucose minus 50 mg/dL | | No adjustment |
| ⬇ | Decrease* | 20% decrease of total dose | Decrease to cover current sensor glucose minus 30 mg/dL | Decrease to cover current sensor glucose minus 75 mg/dL | | No adjustment |
| ⬇⬇ | Decrease* | 30% decrease of total dose | Decrease to cover current sensor glucose minus 60 mg/dL | Decrease to cover current sensor glucose minus 100 mg/dL | | No adjustment |

FIG 3: EXAMPLE GLUCOSE OUTCOMES
Dosing during high rate of change may lead to less optimal glucose outcome
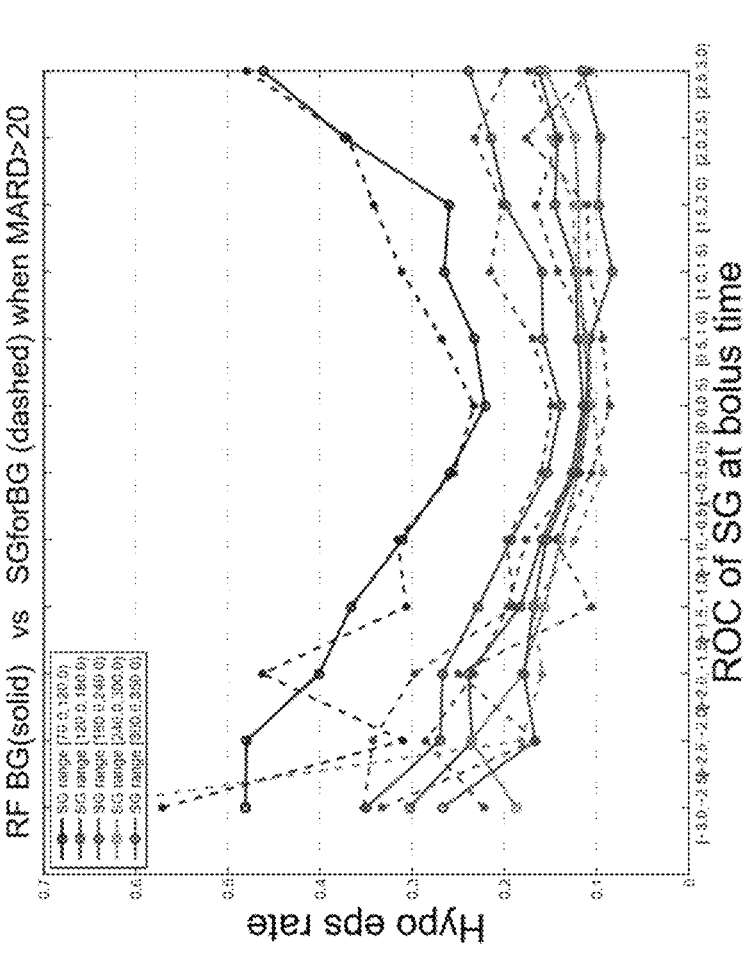

FIG 9: CONCEPT: ENABLING PHYSICIANS TO SET ROC-BASED COMPENSATION

- Update the formula and allow physician to select strategies
- Augment by providing the recommendations to physician or HCP on the setting based on the simulations and algorithm for each patient

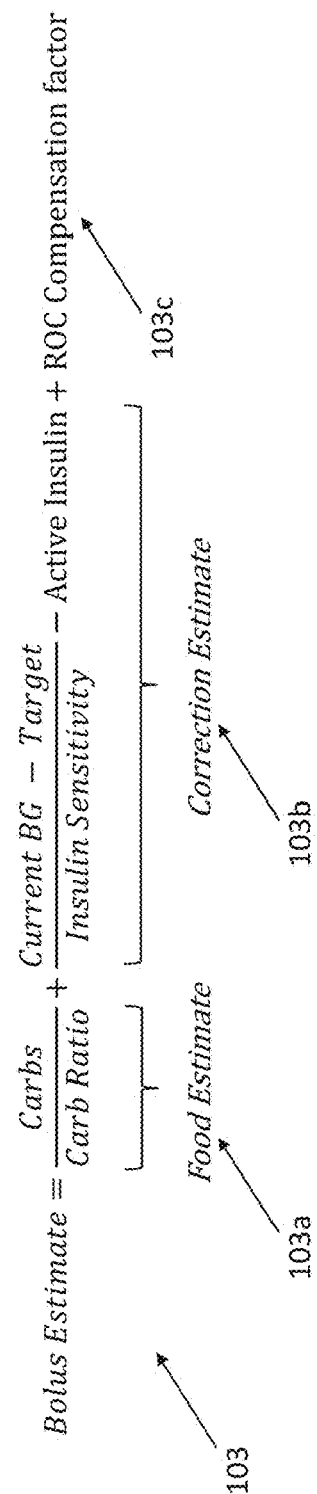

$$Bolus\ Estimate = \underbrace{\frac{Carbs}{Carb\ Ratio}}_{Food\ Estimate} + \underbrace{\frac{Current\ BG\ -\ Target}{Insulin\ Sensitivity} - Active\ Insulin + ROC\ Compensation\ factor}_{Correction\ Estimate}$$

103

103a

103b

103c

FIG 10: IMPROVING ROC CALCULATION FROM DISCRETE TO CONTINOUS

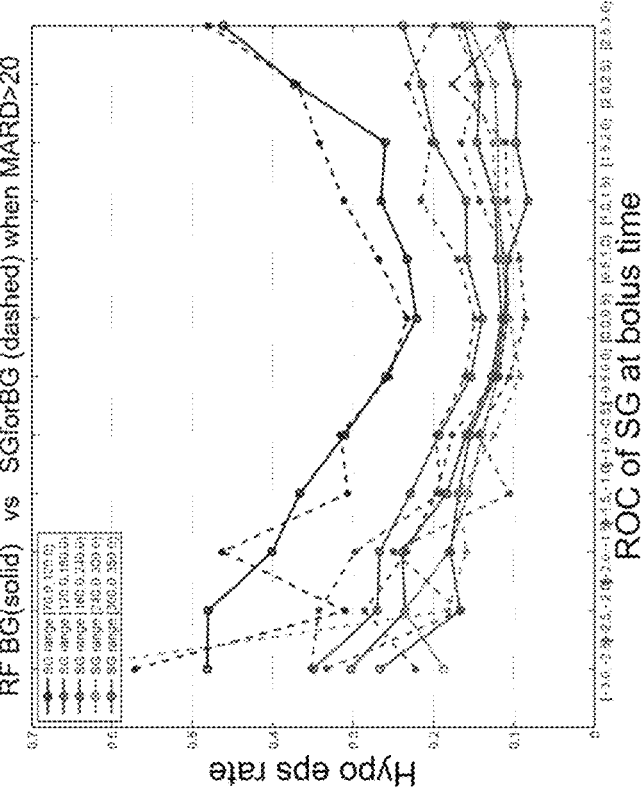

- ROC may be updated manually and discretely based on arrows indicating only directional trend and estimated magnitudes.

- A continuous mapping function converting ROC values to appropriate compensation could create finer adjustments to bolus estimate.

- One method of adjustment could be static adjustment lookup table based on population data collected and tabulated.

- Another method could be to create dynamic variable based on the historical ROC based outcomes for users with specific controls

- The ROC compensation function could also be applied separately to Food Estimate and correction estimate to provide bolus estimate values

FIG 11: COMPENSATION USING CONTINUOUS GLUCOSE PREDICTION

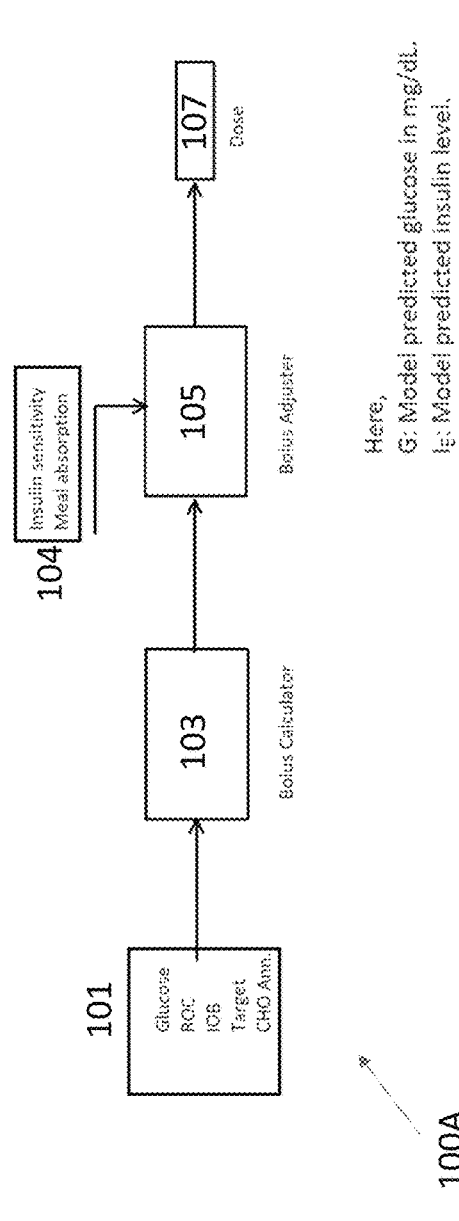

Bolus Adjuster:

The purpose of the bolus adjuster is to use a physiological model to predict future glucose and adjust the dose level accordingly to prevent hypo/hyperglycemic event.

$$\frac{dG}{dt} = -k_G * G\,(t) - S_I * I_E\,(t) + G_L + b_{av} * R_M\,(t)$$

Here, $G$: Model predicted glucose in mg/dL.

$I_E$: Model predicted insulin level.

Insulin PK profile can start with population parameters, but with additional data it can adapt to more patient specific PK profile.

$G_L$: Liver glucose production $R_M$: Rate of appearance of glucose from meal $S_I$: Insulin sensitivity.

$S_I$ can be initialized with TDD, but with additional data it can fine-tuned further.

$k_G$: Glucose clearance rate $b_{av}$: Bioavailability of meal.

Bioavailability and meal absorption time constants can learn based on historical data (day of the week, time of the day, etc.)

FIG 12: COMPENSATION USING CONTINUOUS GLUCOSE PREDICTION
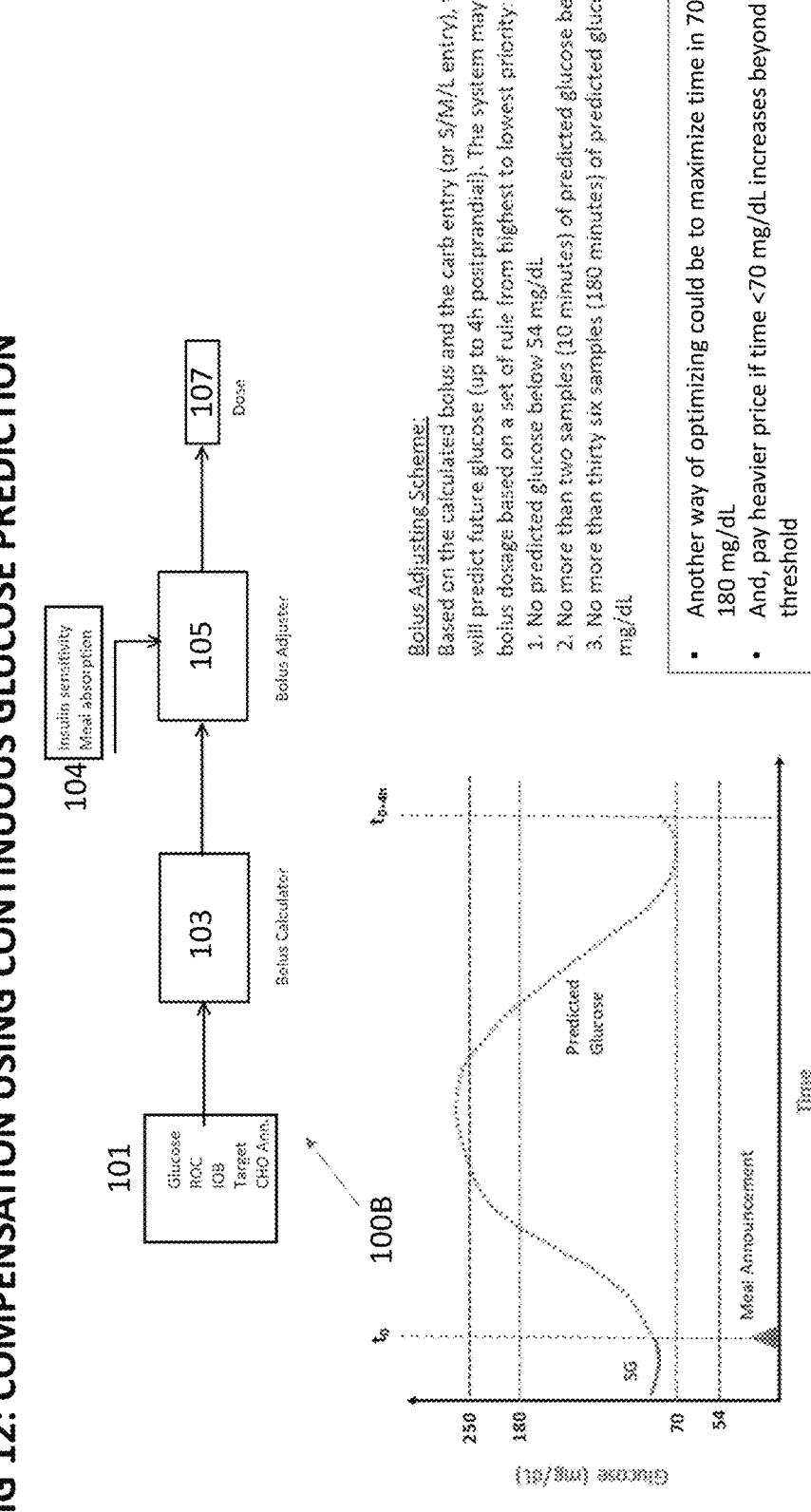

FIG 13: Dynamically setting dosing target using ROC

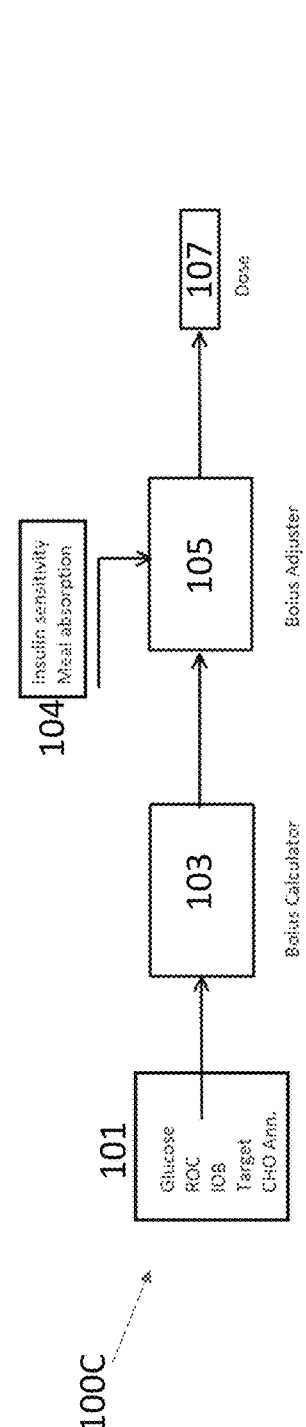

100C

101 — Glucose, ROC, IOB, Target, CHO Ann.

103 — Bolus Calculator

104 — Insulin sensitivity, Meal absorption

105 — Bolus Adjuster

107 — Dose

Bolus Calculator:

The purpose of this module is to calculate the correction and/or meal bolus based on the inputs defined in the above diagram.

$$CB = \begin{cases} If\ G > T(ROC), & \dfrac{G - T(ROC)}{ISF} - IOB \\ Else, & \dfrac{G - T(ROC)}{ISF} \end{cases}$$

$$MB = \frac{CHO}{CR}$$

$$B = CB + MB$$

$$T(ROC) = \begin{cases} If\ ROC < 0, & \overline{T} + d_iT \\ Else, & \overline{T} - d_eT \end{cases}$$

$$Min \le T(ROC) \le Max$$

Here,

CB: Correction bolus in units.

G: Glucose value in mg/dL either from CGM or BG-meter by the user. Can be a zero input.

ISF: Insulin sensitivity factor in mg/dL/ U of the user (can be manually updated or updated by an algorithm)

T(ROC): Target in mg/dL as set by the user. The Target could be a function of ROC (rate of change of glucose). Further details of this function is given below.

IOB: Active insulin in units (decay rate is adjusted by the action speed - which can be manually adjusted or by an algorithm).

MB = Meal bolus in units.

CHO: Carb input by the user in g. Or, this could be a qualitative announcement, such as S/M/L/XL carb. Can be a zero input.

CR: Carb to insulin ratio in g/U.

B: Final bolus amount in units calculated by the bolus calculator.

$\overline{T}$: User settable target in mg/dL delT: Delta target to be added or deducted based on ROC in mg/dL Min, Max: Constraints on the target in mg/dL.

Figure 14:
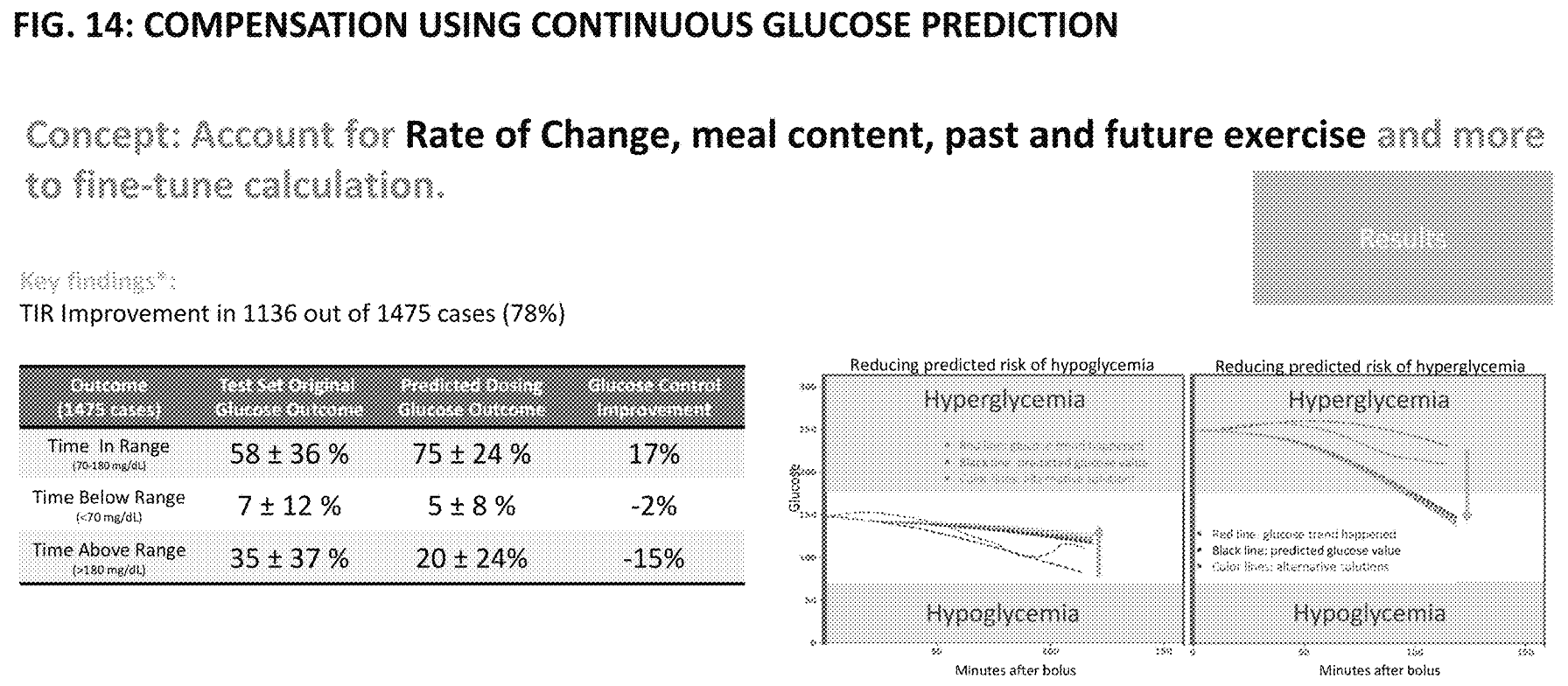

FIG. 14: COMPENSATION USING CONTINUOUS GLUCOSE PREDICTION

Concept: Account for Rate of Change, meal content, past and future exercise and more to fine-tune calculation.

Key findings:

TIR Improvement in 1136 out of 1475 cases (78%)

FIG. 15
USE GESTURE RECOGNITION (GR) WITH ROC

Experiments needs:
- Pre-curser dose strategy
  - o Fixed
  - o Meal estimation
  - o Carb counting
- Remedial dose strategy
  - o Food
  - o Walk
  - o Dose
  - o Wait vs. action User feedback needs:
- How often do users take meals according to plan vs. not
- What are users currently doing when the meal is not according to the plan
- Remedial options preference Remedial Plan Recommendation Eat a bit Take a walk Take correction GR detecting actual carb & macro taken Meal End Pre-curser Dose Meal Start Predicting the carb Glucose

FIG. 16 END TO END MACHINE LEARNING MODEL FOR DOSE RECOMMENDATION WITH SAFETY NET
Could include ML model that utilizes current SG, ROC, IOB, COB as inputs to run a population and/or personalized model to produce an improved recommend bolus dose or ROC compensation to achieve improved outcome
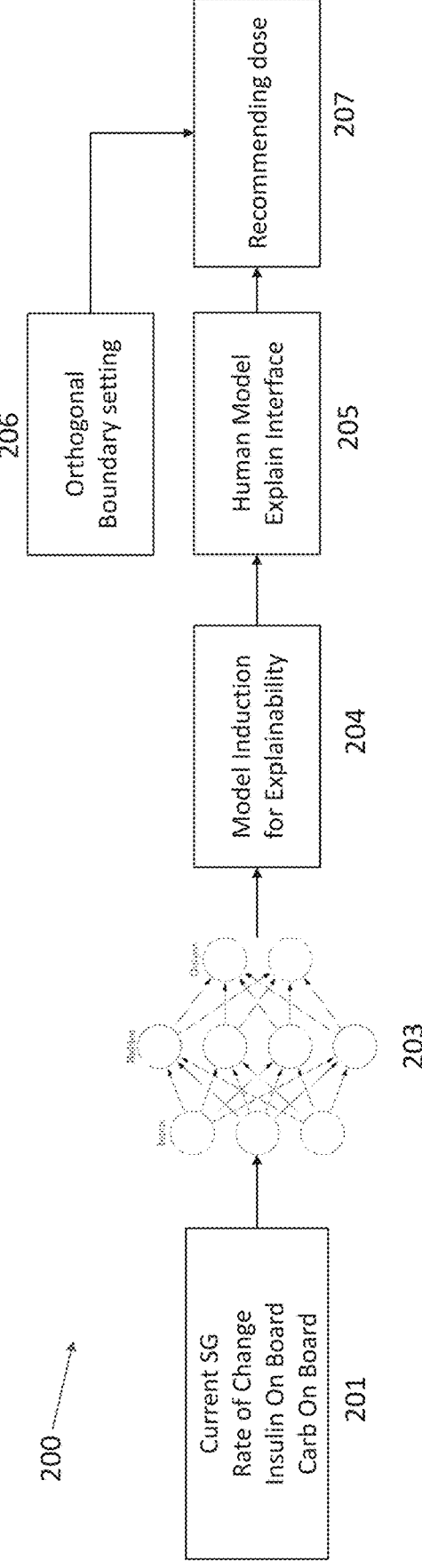

SYSTEMS AND METHODS FOR OPTIMIZING MEDICAMENT DOSING

CROSS REFERENCE TO RELATED APPLICATIONS

This application claims the benefit of the filing date of provisional U.S. Patent Application No. 63/119,720, filed Dec. 1, 2020.

TECHNICAL FIELD

The disclosure relates to medical systems and, more particularly, to medical systems for monitoring and/or managing diabetes.

BACKGROUND

A patient with diabetes receives insulin from a pump or injection device to control the glucose level in his or her bloodstream. Naturally produced insulin may not control the glucose level in the bloodstream of a diabetic patient due to insufficient production of insulin and/or due to insulin resistance. To control the glucose level, a patient's therapy routine may include dosages of basal insulin and bolus insulin. Basal insulin, also called background insulin, tends to keep blood glucose levels at consistent levels during periods of fasting and is a long acting or intermediate acting insulin. Bolus insulin may be taken specifically at or near mealtimes or other times where there may be a relatively fast change in glucose level, and may therefore serve as a short acting or rapid acting form of insulin dosage. Dosages of insulin may be informed, in some instances, by a glucose monitor, which may include, but is not limited to, a continuous glucose monitor (CGM). There exists a need specifically for a glucose monitor or CGM device and associated systems that may leverage communication with a patient to measure physiological parameters such as blood glucose status, and systems capable of optimizing medicament dosages (such as insulin dosages) in response to more holistic inputs that may include a variety of sensor inputs, patient inputs, physician inputs and stored input parameters.

SUMMARY

Devices, systems, and techniques for managing glucose level and other physiological parameters in a patient are described. Medical devices (e.g., pump or injection device) may be in communication with, or otherwise use sensor devices having electrodes to perform various measurements for a patient. Such medical devices may include, for example, a percutaneous cannula configured to deliver insulin to the patient or hand-held injection devices, such as smart insulin pens or disposable insulin pens. The sensor devices having electrodes may concurrently monitor the patient's response to treatment introduced by such medical devices, however, sensor devices (including but not limited to a CGM), may be located on a patient's body at a position optimized for diabetes treatment. The sensor devices and medical devices may exist in a communication network (wired or wireless) with one or more processors and/or patient devices (such as a patient's smartphone equipped with an application or other software) to create an overall system for monitoring a patient disease state and for facilitating treatment thereof. Facilitating therapy may comprise communicating the optimized insulin dose to one or more pumps or injection devices (such as smart injection pens or smart caps for injection pens) that may also be in communication with the one or more processors, sensor devices, and/or patient devices. However, existing systems may be improved to better facilitate optimized treatment of a given patient or group of patients in a given demographic based on various inputs and correction factors that may be received and/or generated by the system.

The techniques of this disclosure include a system for monitoring a patient to optimize medicament dosing, wherein the system comprises one or more processors. In one example the system comprises a patient device (such as a smartphone or other device). In some embodiments, system is configured to receive, using the patient device, an input, the input being indicative of a blood glucose status of the patient, and determine, using one or more processors, an initial insulin dose for the patient based on the input. The system may further optimize, using the one or more processors, the initial insulin dose for the patient, based at least in part on a correction factor received by the one or more processors to create an optimized insulin dose for the patient. The system may also facilitate therapy, using the one or more processors, based on the optimized insulin dose. Facilitating therapy may comprise communicating the optimized insulin dose to one or more pumps or injection devices that may be in communication with the one or more processors, sensor devices, and/or patient devices.

In another example, this disclosure describes a system for monitoring a patient to optimize medicament dosing wherein the system comprises one or more processors and a sensor device implemented in circuitry. The system is configured to measure, using the sensor device, a blood glucose status of the patient, and determine, using one or more processors, an initial insulin dose for the patient based on the blood glucose status of the patient. The system also optimizes, using the one or more processors, the initial insulin dose for the patient, based at least in part on a correction factor received by the one or more processors to create an optimized insulin dose for the patient, and facilitates therapy, using the one or more processors, based on the optimized insulin dose. Facilitating therapy may comprise communicating the optimized insulin dose to one or more pumps or injection devices that may be in communication with the one or more processors, sensor devices, and/or patient devices.

In another example this disclosure describes a method for monitoring a patient to optimize medicament dosing. The method comprises measuring, using a sensor device implemented in circuitry, a blood glucose status of the patient and determining, using one or more processors that may be in communication with the sensor device, an initial insulin dose for the patient based on the blood glucose status of the patient. The method further comprises optimizing, using the one or more processors, the initial insulin dose for the patient, based at least in part on a correction factor received by the one or more processors (via the sensor device, or in other embodiments a patient device that may also be in communication with the one or more processors) to create an optimized insulin dose for the patient. The method also comprises facilitating therapy, using the one or more processors, based on the optimized insulin dose. Facilitating therapy may comprise communicating the optimized insulin dose to one or more pumps or injection devices that may also be in communication with the one or more processors, sensor devices, and/or patient devices.

The details of one or more aspects of the disclosure are set forth in the accompanying drawings and the description below. Other features, objects, and advantages of this disclosure will be apparent from the description and drawings, and from the claims.

BRIEF DESCRIPTION OF DRAWINGS

FIG. 1 is an exemplary therapy dosage determination method.

FIG. 2 is an exemplary therapy dosage determination and revision method.

FIG. 3 is an exemplary depiction of response to some exemplary therapy dosage revision methods.

FIG. 9 is an exemplary therapy dosage determination and optimization method, in accordance with one or more examples described in this disclosure.

FIG. 10 is a depiction of theoretical results using a therapy dosage determination and optimization method, in accordance with one or more examples described in this disclosure.

FIG. 11 is a flow chart illustrating an example process for using continuous glucose prediction for determining and optimizing a therapy dosage, in accordance with one or more examples described in this disclosure.

FIG. 12 is a flow chart illustrating an example process for using continuous glucose prediction for determining and optimizing a therapy dosage, in accordance with one or more examples described in this disclosure.

FIG. 13 is a flow chart illustrating an example process for using rate of change of glucose (ROC) for determining and optimizing a therapy dosage, in accordance with one or more examples described in this disclosure.

FIG. 14 is a depiction of theoretical results using a therapy dosage determination and optimization method using multiple correction factors, in accordance with one or more examples described in this disclosure.

FIG. 15 is a depiction of theoretical results using a therapy dosage determination and optimization method using multiple correction factors, including gesture recognition, in accordance with one or more examples described in this disclosure.

FIG. 16 is a flow chart illustrating an example process for using machine learning techniques for determining and optimizing a therapy dosage, in accordance with one or more examples described in this disclosure.

DETAILED DESCRIPTION

Figure 4:
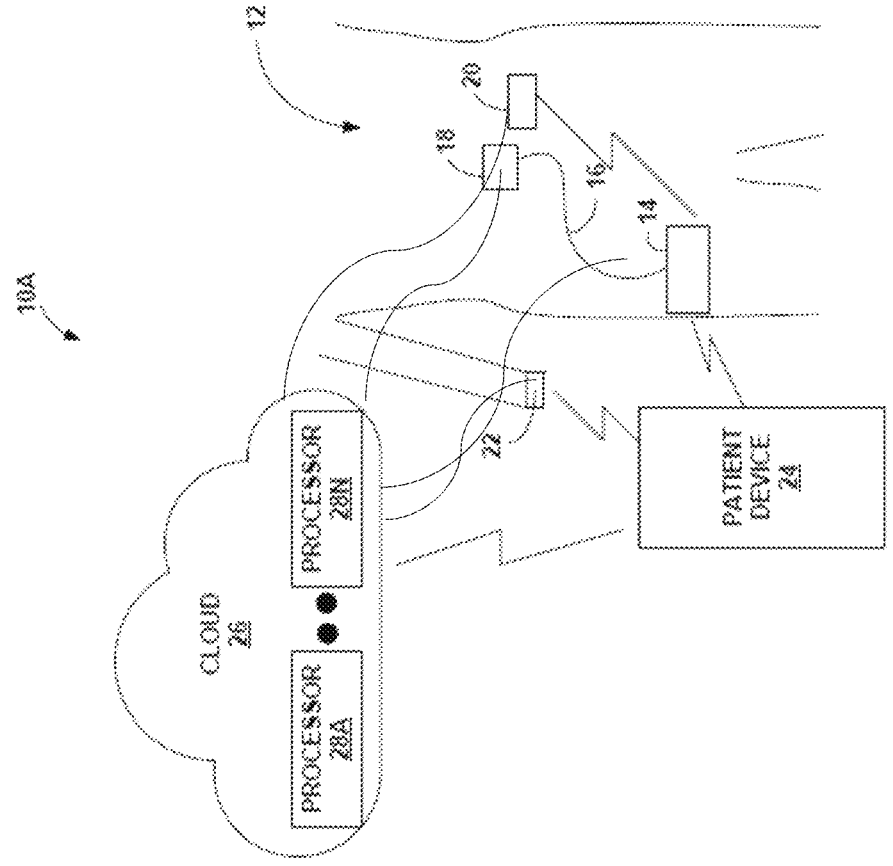
FIG. 4 is a block diagram illustrating an example system for delivering or guiding therapy dosage, in accordance with one or more examples described in this disclosure.

Devices, systems, and techniques for monitoring a glucose level in a patient and optimizing medicament dosing are described in this disclosure. External or implantable medical devices may use electrodes to perform various measurements for a patient. For example, a continuous glucose monitoring (CGM) device may include electrodes to perform glucose sensing. Medical devices, such as the CGM device, may perform sensing functions to detect a blood glucose status of a patient. In other instances, a blood glucose status of a patient may be received by a patient device and/or wearable device, as an input to a dose calculation that may be used to facilitate therapy (such as the administration of a medicament, including, but not limited to an insulin product).

According to various embodiments herein, systems and methods are provided to determine an initial insulin dose for a patient based on the input. This determination may be made by one or more processors resident in an overall system (which may be in communication via a cloud or present in one or more devices in the system). The various embodiments described herein also provide for optimization of the initial insulin dose for the patient, based at least in part on a correction factor received by the one or more processors to create an optimized insulin dose for the patient, and steps for facilitating therapy based on the optimized insulin dose.

FIG. 1 shows one example of a bolus calculator method for insulin delivery to facilitate therapy for a patient with diabetes. The elements of FIG. 1 could serve as one example of a As noted, bolus calculator methods are often based on a blood glucose value (BG) that may be obtained from a single point in time and perhaps based on a sample of a patient's blood recovered using a finger stick and analyzed using a BG strip and analysis device. Bolus estimates may be calculated in some instances, by adding a food estimate to a correction estimate. For example, the food estimate may comprise a ratio of carbohydrates (carbs) to carbohydrate ratio (carb ratio). The correction estimate may first comprise subtracting a measure of active insulin from a correction ratio comprising a difference between current blood glucose (BG) and a target BG for a given patient (which may be prescribed or set by the patient's physician), divided by a measure of insulin sensitivity for the given patient (which may comprise or be modified by a insulin sensitivity factor (ISF) developed by a physician or through other means, for a given patient).

In some instances, rough indications of glucose trend (as indicated by directional and gross or relative magnitude) may be used to inform, modify, or change a percentage of insulin dose or change an absolute insulin dose (by number of units (U), for example). The modifications to insulin dose or blood glucose targets (and/or BG value) may be informed by various pre-set rules corresponding to the rough indications of glucose trend as shown in the various examples of glucose trend indications (as indicated by "trend arrows") and resulting insulin and glucose value adjustment examples are shown in FIG. 2. As can be seen in FIG. 2, some examples create insulin dosing scenarios during high rate of change (ROC) periods for blood glucose.

FIG. 3 illustrates illustrative or potential glucose outcomes for patients whose therapy (dosing) may be informed by high BG ROC periods.

CGM devices (such as, for example, a sensor device 20 depicted in the various embodiments herein) may also potentially be used to augment and/or improve bolus calculators using continuous blood glucose values. In addition, there exist opportunities to improve bolus calculators or therapy "wizard" software to facilitate therapy by considering blood glucose trend data or other data to create a correction factor in the formula. The data informing a correction factor could include, but are not limited to, population data stored in the cloud 26, personalized data stored in or derived from the cloud 26, a patient device 24 or wearable device 22, data indicative of past or ongoing therapy regimes stored in or derived from an insulin pump 14 or injection device 30, and/or combinations of such data and data sources.

FIG. 9 shows an alternate example of a bolus calculator 103 method for insulin delivery to facilitate therapy for a patient with diabetes. The bolus calculator 103 methods of FIG. 1 and FIG. 9 are examples of bolus calculator 103 element shown in the system and method embodiments 100A, 100B, and 100C of FIG. 11, FIG. 12 and FIG. 13, respectively. In the exemplary embodiment of FIG. 9, the bolus calculator 103 shown may include a correction factor that may be input by a physician (such as the ROC Compensation factor 103c). In this example, the bolus calculator 103 is allows for direct augmentation and allows the physician to select therapy strategies pursuant to their direct guidance for a specific patient that may, in some instances, be based on empirical data for a given patient 12 (such as the patient's known weight, insulin sensitivity, diet, nutrition habits, and activity level). The various systems 10A, 10B and 10C may also provide recommendations to a physician or other health care provider (HCP) for the appropriate ROC Compensation factor 103c or other correction factor based on simulations and algorithms for each patient 12 wherein aggregated data (stored in the cloud 26, for example) may be based on a cluster of patient data indicating a similar profile to a given patient 12 (such as body mass index (BMI), insulin sensitivity factor (ISF), insulin-to-carbohydrate ratio (ICR) or other profile data) to arrive at a particular dose 107 for facilitating therapy (as shown, for example, in systems 100A, 100B, 100C).

FIG. 10 shows methods by which the ROC compensation factor 103C for bolus calculation 103 can also be calculated as a correction factor based on continuous mapping functions converting ROC values (received by processors 28, for example, from a sensor device 20 such as a CGM) to an appropriate ROC compensation factor 103C to create finer adjustments to a dose recommendation 107 or other bolus estimate. One method of ROC compensation factor 103c determination or other adjustment to the bolus calculator 103 could be a static adjustment lookup table based on population data collected and tabulated in processors 28 in the cloud 26. In another example, an appropriate ROC compensation factor 103c could be a dynamic variable based on historical ROC-based outcomes for patients with specific controls. The ROC compensation factor 103c could also be applied separately to different components of the bolus calculator 103 shown on FIG. 9, including, but not limited to the food estimate 103a and the correction estimate 103b to provide more accurate and efficient bolus estimate values (see dose 107, for example, in FIG. 11).

In various other embodiments the dose calculator 103 can incorporate a number of glucose prediction-based adjustments or correction factors 103c to arrive at an optimized dose 107. For example, using continuous glucose prediction, in lieu of the directional arrow indications described in FIG. 2, to optimize dose 107. The ROC compensation factor 103c could also be created using a continuous glucose cone (predicted glucose with uncertainties), instead of a single trace, to optimize dose 107. ROC compensation factor 103c may also be created using continuous glucose prediction that is sensitive to other inputs or correction factors that may be received by a patient device 24, wearable device 22, processor 28 or other component of a system 10A, 10B, 10C. Such inputs or correction factors may include, but are not limited to, future planned exercise, meals, travelling schedules, gestures indicative of activity, eating, or drinking detectable by an application or other software module. Overall, the ROC compensation factor 103c may provide physicians and patient 12 many different options for calculating an optimal dose 107 or otherwise facilitating therapies that are based on future conditions, using a range of factors suitable for the needs of a given patient 12, from conservative therapy plans to more aggressive therapy plans if many factors affecting a blood glucose factor may be in play. While the ROC compensation factor 103c is shown generally as a component of the bolus calculator 103 component, it should be understood that the ROC compensation factor may also comprise a correction factor 104 or other component or input to the bolus adjuster 105 or steps or a method or system 10A for optimizing, using the one or more processors 28A . . . 28N, or 28, more generally, the initial insulin dose for the patient 12, based at least in part on a correction factor 104 received by the one or more processors 28 to create an optimized insulin dose 107 for the patient 12.

Referring generally to FIG. 11, the operation of an exemplary system 10A, 10B, or 10C, and exemplary method 100A is shown for monitoring a patient to optimize medicament dosing (such as an insulin dose 107). In one embodiment, the system 10A may comprise one or more processors 28A . . . 28N and a patient device 24 implemented in circuitry (see, for example, FIG. 7) and/or a sensor device 20 implemented in circuitry (see, for example FIG. 8). In one embodiment, the system 10A may be configured to receive, using the patient device 24 or a similar wearable device 22, an input 101, the input 101 being indicative of a blood glucose status of the patient. In other embodiments, the system 10A may be configured to receive the input 101 indicative of a blood glucose status of the patient 12 using a sensor device 20 (such as a CGM or other wearable medical device). The input 101 may comprise a number of different data, including but not limited to, blood glucose level, continuous glucose measurements, rate of change (ROC) of blood glucose, active insulin or "insulin on board" (IOB), target glucose prescribed by a physician and input via processors 20A . . . 28N or other devices in communication with the cloud 26, carbohydrates annotated by a patient 12 via patient device 24 or wearable device 22, or other inputs 101 that may be created, detected, input, or processed by various components of the systems 10A, 10B, 10C described herein, including but not limited to: a continuous rate of change of blood glucose of the patient 12 as measured by the sensor device 20, a blood glucose measurement of the patient 12 as measured by the sensor device 20 (such as a CGM), or another indication of blood glucose or other physiological measurement received by any of the various components of systems 10A, 10B, 10C described herein and their various processing units, sensors, transducers, and/or user interfaces.

FIG. 11 also shows generally steps or operations for system 10A, 10B, or 10C for determining, via bolus calculator 103, for example, using one or more processors 28, an initial insulin dose for the patient 12 based on the input 101 (which may comprise a blood glucose status of a patient 12). The determining step 103, may comprise one or more of the dose calculators 103 described herein with respect to FIG. 1, FIG. 9, or FIG. 10 and other embodiments, or other dose calculation methods known to endocrinologists or other healthcare professionals (HCPs) that may be implemented and/or optimized using processing techniques and housed in processors 28. The system 10A may also implement steps or operations for optimizing, using the one or more processors 28, the initial insulin dose (which may include, but is not limited to, an output of a dose calculator 103) for the patient 12, based at least in part on a correction factor 104 received by the one or more processors 28 to create an optimized insulin dose 107 for the patient 12. The system 10A may also implement various steps or operations for facilitating therapy, using the one or more processors 28, based on the optimized insulin dose 107. For example, in some embodiments, the optimized insulin dose 107, may be displayed on a patient device 24 or wearable device 22, or smart injection device 30 (as shown in the system of 10C in FIG. 6) to inform a patient of an optimized dose 107 that the patient 12 may then utilize to apply (for example, by selecting a corresponding number of insulin units) the optimized dose to effect their therapy using an appropriate or selected medicament dispensing device which may include, but is not limited to, an insulin pump 14, a smart injection device 30, syringe, or injection pen.

FIG. 11 also shows the operation of an exemplary optimization step 105 or "bolus adjuster" method step that may be undertaken by processors 28A . . . 28N of systems 10A, 10B, or 10C or processing circuitry present in the sensor device 20, patient device 24, wearable device 22, or various other components in addition to an initial determination step 103 (such as the initial bolus calculators 103 shown in FIG. 1 and FIG. 9 for example). In some embodiments, the optimization step 105 uses a physiological model to predict future glucose and adjust the dose level 107 or otherwise facilitate therapy accordingly to prevent hypoglycemic or hyperglycemic events in a patient 12 with diabetes. In such embodiments, G is model-predicted glucose expressed in mg/dL, and $I_E$ is model-predicted insulin level (where insulin pharmacokinetic profile may start with population parameters stored in cloud 26, but with additional data such as correction factors 104 or additional inputs 101, it may adapt to a more-patient specific pharmacokinetic profile. $G_L$ comprises a measure of liver glucose production, and $R_M$ comprises a measure of the rate of appearance of glucose from a meal (which may be derived from a GR application, PUI, or a patient 12 input 101 to an application or other software resident on a patient device 24, for example). $S_I$ represents insulin sensitivity in this example for the patient 12, and it may be initialized with TDD, but with additional inputs 101 or correction factors, it may be "fine-tuned" for a specific profile of patient 12. Finally, $k_G$ represents a glucose clearance rate for a specific patient 12 or patient profile, and $b_{AV}$ represents the bioavailability of a meal, which may be "learned" by the system 10 based on historical data associated with a patient 12 or a patient profile stored in the cloud 26 such as day of the week, time of the day, etc. In this example, the various inputs 101 and/or correction factors 104 may be used in this optimization step 105 or "bolus adjuster" to approximate a value of glucose over time (dG/dt) in order to augment or optimize the initial dose calculation or determination step 103, where, as shown in FIG. 11:

$$dG/dT = k_G * G(t) - S_I * I_E(t) + G_L + b_{AV} * R_M(t).$$

FIG. 12 shows the operation of an alternate exemplary optimization step 105 or "bolus adjusting scheme" method step that may be undertaken by processors 28A . . . 28N of systems 10A, 10B, or 10C or processing circuitry present in the sensor device 20, patient device 24, wearable device 22, or various other components in addition to an initial determination step 103 (such as the initial bolus calculators 103 shown in FIG. 1 and FIG. 9 for example). In this example, based on the calculated or determined initial dose from step 103, and an another input 101 comprising a carbohydrate entry or small/medium/large meal entry (which may be estimated by a GR software or PUI, such as the KLUE™ application available from Klue, Inc. and Medtronic Min-iMed, Inc.), the optimization step 105 may predict future glucose (up to 4 hours postprandial (post-mealtime). In addition, the optimization step 105 model in this example may adjust or optimize the eventual bolus dosage 107 based on a set of rules (that may comprise an additional correction factor 104 input by patient 12 or patient's physician via the cloud 26). The rules in this example may be prioritized according to the ranking set forth as: 1. No predicted glucose below 54 mg/dL; 2. No more than two samples (10 minutes) of predicted glucose below 70 mg/dL; and 3. No more than thirty-six samples (180 minutes) of predicted glucose above 260 mg/dL. In other examples, the optimizing step 105 may also operating using correction factors 104 or other inputs 101 to maximize time in a predicted blood glucose range between approximately 70 and 180 mg/dL, and intensify therapy facilitation 107 or supplemental dose 107 if time of predicted blood glucose lingers in a range less than 70 mg/dL for a time that exceeds an threshold input by the patient 12 or patient's physician. A example plot of predicted glucose in mg/dL over time after a "meal announcement" (which may be an input from a GR software, for example) is shown with example range guard rails in FIG. 12 to inform the optimization step 105 or "bolus adjusting scheme" in this example.

FIG. 13 shows an example for dynamically facilitating therapy (for example an optimal dose 107 target) using blood glucose rate of change (ROC), as sensed, for example by various components of a system. In the example of FIG. 13, the dose determination step 103 or "bolus calculator" is optimized using direct inputs 101 comprising ROC and other inputs 101 and correction factors 104 as follow, wherein: CB is a correction bolus in units of insulin; G is a glucose value in mg/dL from a sensor device 20 (such as a CGM) or a blood glucose meter reading input by the patient 12 or other user into the system 10; and ISF is an insulin sensitivity factor in mg/dL/U that is determined for a particular patient 12 or patient profile derived from population data in the cloud 26, wherein ISF may be manually updated or updated by an algorithm resident in the system 10. T(ROC) is a target glucose level as a function of ROC as set by the patient 12 or a patient's physician. T(ROC) may be a function of ROC of glucose. IOB is active "insulin on board" in units (wherein decay rate is adjusted by the action speed of a particular patient 12 or patient profile derived from population data in the cloud 26). MB is a meal bolus in units (which may be a defined input 101 input by patient 12 or patient's physician). CHO is carbohydrate input by the user in grams. CHO may also be a qualitative input 101 by the patient into the system 10 using a patient device 24 (such as a designation of S/M/L/XL carbs). CHO may also be a zero input if no meal announcement is made or if an active GR software (which may also be used to input CHO in the system 10) does not detect a meal or beverage intake using gesture recognition. CR is a carb-to-insulin ratio in g/U for a specific patient 12 or patient profile which may be based on population data stored in the cloud 26 and optimized by processors 28A . . . 28N. B is a final bolus amount in units calculated by the bolus calculator. Furthermore, $\overline{T}$ is a user or patient 12 settable target expressed in mg/dL, delT is a delta or change target to be added or subtracted from a value based on ROC expressed in mg/dL, and "Min, Max" represent constraints on the target T̄ expressed in mg/dL. In such embodiments, the bolus calculator 103 functions may be expressed as follows:

Bolus Calculator:

The purpose of this module is to calculate the correction and/or meal bolus based on the inputs defined in the above diagram.

$$CB = \begin{cases} \text{If } G > T(ROC), & \dfrac{G - T(ROC)}{ISF} - IOB \\ \text{Else,} & \dfrac{G - T(ROC)}{ISF} \end{cases}$$

$$MB = \dfrac{CHO}{CR}$$

$$B = CB + MB$$

$$T(ROC) = \begin{cases} \text{If } ROC < 0, & \bar{T} + delT \\ \text{Else,} & \bar{T} - delT \end{cases}$$

$$\text{Min} \le T(ROC) \le \text{Max}$$

Referring generally again to FIG. 11, FIG. 12 and FIG. 13, operations of exemplary systems 10A, 10B, or 10C, and exemplary methods 100A, 100B, 100C are shown for monitoring a patient to optimize medicament dosing (such as an insulin dose 107). In one embodiment, a system 10A, 10B, or 10C is provided for monitoring a patient 12 to optimize medicament dosing, wherein the system comprises one or more processors 28A . . . 28N (or processors in circuitry 32, 62 embodied in patient devices 24 (FIG. 7) and sensor devices 20 (FIG. 8), respectively. System 10A, 10B, or 10C may also comprise a sensor device 20 implemented in circuitry, and the system 10A, 10B, or 10C may be configured to perform various steps depicted generally in FIG. 11, FIG. 12 and FIG. 13, including, but not limited to: measuring 101, using the sensor device, a blood glucose status of the patient 12; determining 103, using one or more processors 28A . . . 28N, an initial insulin dose for the patient 12 based on the blood glucose status of the patient 12; optimizing 105, using the one or more processors 28A . . . 28N, the initial insulin dose for the patient 12, based at least in part on a correction factor 104 received by the one or more processors 28A . . . 28N to create an optimized insulin dose for the patient 12, and facilitating therapy 107, using the one or more processors 28A . . . 28N, based on the optimized insulin dose.

In some embodiments, the correction factor 104 comprises a patient input received from a patient device 24 in communication with the one or more processors 28A . . . 28N. As described herein, correction factor 104 comprises a gesture recognized by a gesture recognition (GR) program resident on at least one of the one or more processors 28A . . . 28N including, but not limited to processing circuitry 32 present in patient device 24 (see FIG. 7, for example). The patient input embodying a correction factor 104 or other measurement or other input 101 may comprise an indication of at least one of a type and an amount of food or beverage consumed by the patient 12 as detected by the patient device 24. Patient input embodying a correction factor 104 or other measurement or other input 101 may also comprise an indication of at least one of a type and a duration of exercise performed by the patient 12 as detected by the patient device 24 and/or a wearable device 22 worn by patient and in communication with the system 10A, 10B, or 10C. In some embodiments, the correction factor 104 or other measurement or other input 101 may also comprise a target blood glucose level for the patient 12. The blood glucose status may be a product of the measuring step 101 to create an input comprising a blood glucose measurement (including, but not limited to sensor glucose, blood glucose, sensor glucose rate of change (ROC) of the patient 12 as measured by the sensor device 20. Furthermore, the blood glucose status measurement 101 or input may comprise a continuous rate of change (ROC) of blood glucose of the patient 12 as measured by the sensor device 20.

The rate of change input 101 or correction factor 104 that may be utilized in the various systems 10A, 10B, and 10C, methods 100A, 100B, and 100C and functions described herein may, in some examples be bounded or otherwise constrained based on additional inputs 101 or correction factors 104 to ensure that therapy facilitation steps 107 are optimal for a given patient 12 or patient profile (which may be based on profile or population data stored in the cloud 26). In some such embodiments, the ROC may be constrained by additional correction factors 104 or other inputs 101 that may include, but are not limited to: (1) minimum and maximum ROC compensation inputs 101 or correction factors 104 based on user or patient 12 past success in compensation history that may be stored in the processors 28A . . . 28N of the systems and/or in memory components present in the patient device 24, wearable device 22, and/or sensor devices 20; (2) settings for the minimum and maximum ROC compensation inputs 101 or correction factors 104 by a patient's physician that may be stored in the processors 28A . . . 28N of the systems and/or in memory components present in the patient device 24, wearable device 22, and/or sensor devices 20; and/or derived or "mined" minimum and maximum ROC compensation inputs 101 or compensation factors 104 through user or patient 12 experience level or other patient 12 history saved in or derived from various components of a system 10A, 10B, and/or 10C.

The rate of change input 101 or correction factor 104 that may be utilized in the various systems 10A, 10B, and 10C, methods 100A, 100B, and 100C and functions described herein may, in some examples be augmented or otherwise optimized (see step 105, for example) based on different inputs 101 or correction factors 104 such as "look ahead" windows to ensure that therapy facilitation steps 107 are optimal for a given patient 12 or patient profile (which may be based on profile or population data stored in the cloud 26). In some such embodiments, the ROC may be constrained by additional correction factors 104 or other inputs 101 that may include, but are not limited to: (1) shortening ROC time windows for meal times (as reported and/or detected by GR, for example) and longer window for overnight (as reported and/or detected by patient device 24 or wearable device 22, for example) to improve compensation or optimization step 105 accuracy for a patient 12; (2) from data stored in cloud 26 or elsewhere in system 10, deriving how long the current ROC will last (using, for example, ROC of ROC or help of a "virtual patient" model derived from population data stored in the cloud 26); and/or (3) modifying the ROC-based adjustment amount based on time of day (as reported or detected, for example, by patient device 24, wearable device 22 and/or other components of system 10).

The rate of change input 101 or correction factor 104 that may be utilized in the various systems 10A, 10B, and 10C, methods 100A, 100B, and 100C and functions described herein may, in some examples be augmented or otherwise optimized (see step 105, for example) based on different inputs 101 or correction factors 104 such as relatively empirical inputs. For example, systems 10A, 10B, and 10C may discern the impact on sensor glucose (taken from a sensor device 20, for example) ROC for different meal types using a nutrition insights platform application (such as Nutrino™, available from Medtronic MiniMed, Inc. for example) food or dietary logs that may be stored in the cloud 26 and/or memory components of patient device 24 or wearable device 22. In other embodiments, systems 10A, 10B, and 10C may also mine impact on sensor glucose ROC for different exercises or other physical activity (i.e. low, medium and high intensity activity) from taken from activity tracker data from a wearable device 22, for example. In other embodiments, systems 10A, 10B, and 10C may make modifications of insulin dose adjustments (facilitating therapy 107, for example) using mined data as correction factors 104 for future boluses. Systems 10A, 10B, and 10C may also make insulin dose adjustment (i.e. optimizing 105, for example) using historically similar ROC adjustments taken as a correction factor 104 (a "nearest-neighbor" process, for example). Systems 10A, 10B, and 10C may also make insulin dose 107 adjustment (optimization 105, for example) using ROC based on prioritized outcomes set by patient 12 or physician or other HCP for a patient. Systems 10A, 10B, and 10C may also use analytics and simulations to mine for an optimized strategy for specific patient 12. In such examples, strategy optimizations 105 may be aggregated in a cloud 26 to be used by systems 10A, 10B, and 10C based on patients with a similar "virtual patient" profile. In other such examples, strategy optimizations 105 may be aggregated in a cloud 26 or in individual systems 10A, 10B, and 10C using empirical data based on individual patient 12 and collected by a patient 12 system 10A, 10B, and 10C over time.

The rate of change input 101 or correction factor 104 that may be utilized in the various systems 10A, 10B, and 10C, methods 100A, 100B, and 100C and functions may, in some examples, be augmented or otherwise optimized (see step 105, for example) based on different inputs 101 or correction factors 104 such as past outcome empirical inputs (usable as correction factors 104, for example). Such "past outcome" empirical inputs, may be used in place of population-based data stored in a cloud 26 (such as a virtual patient (VP) model) in some instances. One potential advantage to "past outcome" use, is that it may not require complete meal logging via GR or other means, to be successful. In one example, a process might include, but is not limited to, the following steps: (1) compare glucose response outcomes and Bolus Wizard (BW) recommendation bias, where the Bolus Wizard (BW) is a feature available on certain systems available from Medtronic MiniMed, Inc. (i.e. the difference between what BW recommends and what that patient 12 takes); (2) Evaluate if the difference from step (1) changes across various factors, including but not limited to: sensor glucose rate of change (SG ROC), sensor glucose level, insulin on board (IOB), carbs on board (COB), time of day (TOD); (3) build a function and/or recommendation rules, in the form of a correction factor 104, for example, for biasing and/or optimizing 105 and facilitating dose 107 boluses based on the current value of the factor(s) found in in step (2). When using this method of optimization 105, a few additional considerations may also be implemented including, but not limited to: (1) glucose outcomes can be time-in-range (TIR), excursion from range events, sensor glucose delta from glucose target, etc.; (2) taking account for or filtering filter cases where the user or patient 12 takes a second bolus 107 or meal during the outcome window.

Empirical data may be noisy in some embodiments and could require threshold amounts of data (perhaps stored in a system 10 cloud 26) in order to generate suitable correction factors 104 and/or personalize optimized therapy facilitation (see steps 105, 107, for example in FIG. 11, FIG. 12, and FIG. 13) for patient 12. However, it may be advantageous to "cluster" patients' 12 data and based on insulin sensitivity factors (ISF), postprandial response, algorithm demonstrations or learning sessions, and/or other factors. If a suitable relationship emerges across empirical data comprising events, system 10 may optimize 105 various therapy facilitation steps 107 (i.e. meal boluses, in one example), review carb counting or review BW settings.

As shown in FIG. 16, in some embodiments, the computing power of systems 10A, 10B, and 10C may be leveraged to implement machine learning (ML) to optimize input 101 or correction factor 104 that may be utilized in the various systems 10A, 10B, and 10C, methods 100A, 100B, and 100C and functions described herein. In one exemplary embodiment, a dose optimization step or calculator 103 or dose optimization step 105 may include a ML model 200 that utilizes current SG, ROC, insulin on board (IOB), carbs on board (COB) and potentially other inputs 201 sensed or stored to run a population and personalized model to produce an optimized recommended bolus dose 207 or, in some examples simply create an appropriate correction factor 104 to be implemented in the various methods shown generally in FIG. 11, FIG. 12 and FIG. 13 to facilitate optimal therapy outcomes for patient 12. In some such embodiments, certain inputs 201 such as current SG, ROC, insulin on board (IOB), carbs on board (COB) and potentially other inputs 101 may enter a ML system 203. The ML model 203 would undergo model explainability step 204 which is further refined by human usability system 205 together with boundary settings for the recommendation 206 would finally present a modified recommended dose 207 to patient . . . .

FIG. 14 depicts the improvement in time in range (TIR) after adjustment in insulin amount based on glucose rate of change, meal content, past and future exercise knowledge in in-silico experiments. some potential results for blood glucose or sensor glucose time in range (TIR) for patients 12 that might use systems 10A, 10B, and 10C or the various methods depicted as elements 100A, 100B, and 100C in FIG. 11, FIG. 12, and FIG. 13, respectively.

Figure 5:
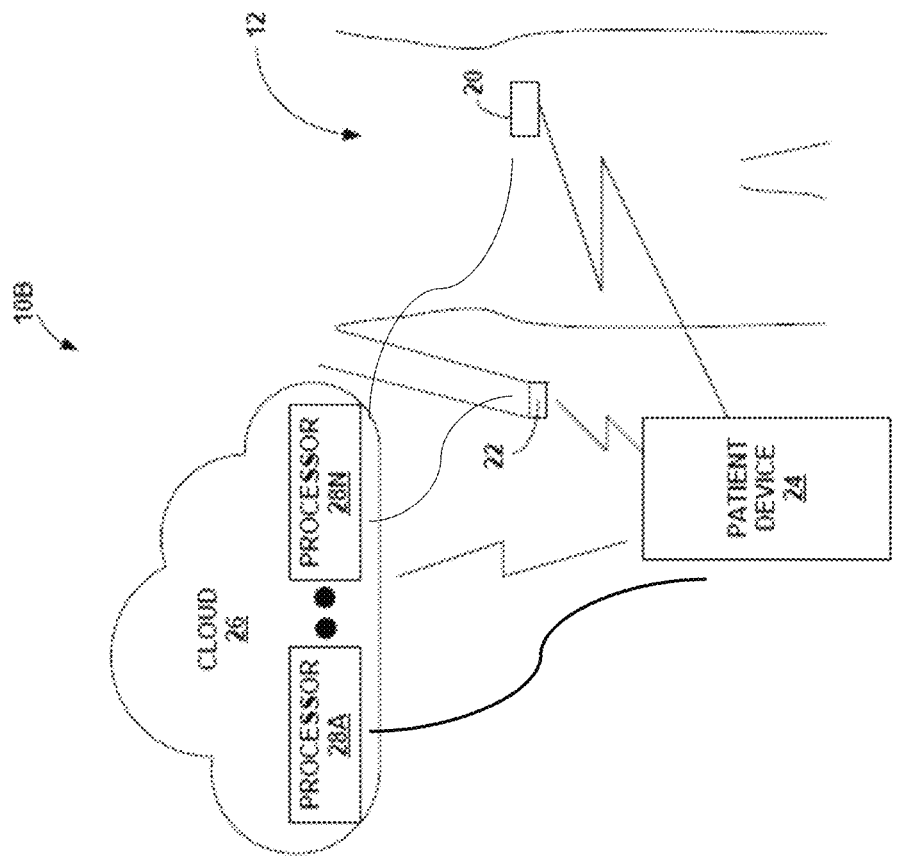
FIG. 5 is a block diagram illustrating another example system for delivering or guiding therapy dosage, in accordance with one or more examples described in this disclosure.
Figure 6:
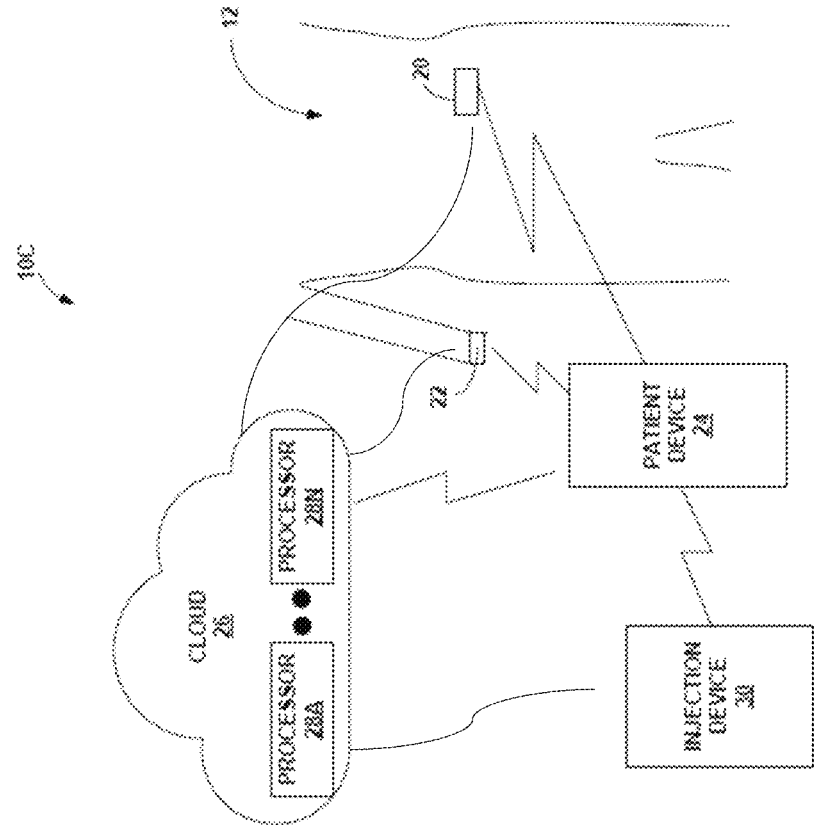
FIG. 6 is a block diagram illustrating another example system for delivering or guiding therapy dosage, in accordance with one or more examples described in this disclosure.

In some embodiments of the various systems 10A, 10B, and 10C, the input 101 comprises a patient input to the patient device 24 or a blood glucose status received, for example, from a sensor device 20. However, inputs (including, but not limited to a patient input) received from a patient 12, a sensor device 20, wearable device 22, patent device 24, processors 28, injection device 30, insulin pump 14, cloud 26, or other components of a system according to various embodiments herein may be used not only as input 101, but also as a correction factor 104, or inputs to inform the bolus calculator 103 (such as a ROC correction factor 103c, as described herein). In some embodiments, an exemplary patient input comprises a gesture recognized by a gesture recognition (GR) program or other perceptual user interface (PUI) (such as, for example, the KLUE™ application available from KLUE, Inc. and Medtronic MiniMed Inc.), resident on an least one of the one or more processors, the circuitry of the patient device 24, and/or any portion of the various systems 10A, 10B, and 10C shown in FIG. 4. FIG. 5, and FIG. 6, respectively.

The various steps or operations for systems 10A, 10B, or 10C (shown in FIG. 4, FIG. 5, or FIG. 6, respectively) may utilize inputs 101 (or patient inputs received via patient device 24 or wearable device 22, for example, comprising an indication of at least one of a type and an amount of food or beverage consumed by the patient 12. Such inputs, may comprise, for example, inputs of a gesture recognition (GR) for detecting the patient consuming a food or beverage (or more generally, a meal). In some such embodiments, the bolus calculator 103 or determining step 103 may be used as a first or second input 101 with the food or beverage indication such that multiple inputs 101 are used to inform the determining step 103. In a first example, if GR detects a meal (first input) and a sensor device 20 engaged with or worn by a patient 12, detects no rate of change (ROC) of blood glucose level of patient 12 (second input), the resulting determining 103 and optimizing 103 steps may result in no or very slight adjustments to the dose or other facilitated therapy step 107. In a second example, if GR detects no meal (first input) and a sensor device 20 engaged with or worn by a patient 12, detects no rate of change (ROC) of blood glucose level of patient 12 (second input), the resulting determining 103 and optimizing 103 steps may also result in no or very slight adjustments to the dose or other facilitated therapy step 107. In a third example, if GR detects a meal (first input) and a sensor device 20 engaged with or worn by a patient 12, detects a rapid decrease in the rate of change (ROC) of blood glucose level of patient 12 (second input), the resulting determining 103 and optimizing 103 steps may also result in no or very slight adjustments to the dose or other facilitated therapy step 107. In a fourth example, if GR detects no meal (first input) and a sensor device 20 engaged with or worn by a patient 12, detects a rapid decrease in the rate of change (ROC) of blood glucose level of patient 12 (second input), the resulting determining 103 and optimizing 103 steps may result in a reduction in the dose or other facilitated therapy step 107. In a fifth example, if GR detects a meal (first input) and a sensor device 20 engaged with or worn by a patient 12, detects a rapid increase in the rate of change (ROC) of blood glucose level of patient 12 (second input), the resulting determining 103 and optimizing 103 steps may result in a relatively high increase in the dose or other facilitated therapy step 107. In a sixth example, if GR detects no meal (first input) and a sensor device 20 engaged with or worn by a patient 12, detects a rapid increase in the rate of change (ROC) of blood glucose level of patient 12 (second input), the resulting determining 103 and optimizing 103 steps may result in a moderate increase in the dose or other facilitated therapy step 107.

FIG. 15 shows one example of a principle of operation of a system 10A, 10B, or 10C utilizing GR inputs 101 along with ROC inputs 101 to perform optimization steps 105 and therapy facilitation 107 (which may or may not include recommending or triggering a medicament dose). In this example, GR is used to receive a first input 101 comprising actual carbohydrates taken as a meal begins (the GR may detect, for example, patient 12 gestures indicating a meal being consumed), which may trigger an initial dose calculation 103, and/or optimization 105 based, for example on a real-time indication of blood glucose ROC (detected, for example, by a sensor device 20). The dose calculation 103 and/or optimization 105 may be further informed by additional correction factors 104 such as a patient-specific factor (ISF, BMI, patient proxy based on population data received by or resident in processors 28A . . . 28N)). Once the GR input 101 indicates mealtime ending, a sensor device 20 may continue to inform the system and monitor the blood glucose status of the patient 12 such that the system (via a patient device 24, wearable 22, or other device of the system 10 capable of interaction or notification) can issue a follow up facilitation of therapy 107 (described here as a "remedial plan recommendation"), comprising, for example, an indication or recommendation to eat or drink (if blood glucose drops near a range which may comprise an input 101 or correction factor 104), to take a walk (if blood glucose remains elevated but is manageable based on patient habits (which may comprise an input 101 or correction factor 104 known or made known to system 10); or to administer a correction dose 107 that may be optimized by a continuous or semi-continuous running of dose calculator 103 and/or optimization steps 105 to ensure that patient maintains an optimized blood glucose status. Thus the multi-input 101 and correction factor 104 usage by the system 10, allows the various systems 10A, 10B and 10C (FIG. 4, FIG. 5 and FIG. 6, respectively) and methods 100A, 100B, 100C (FIG. 11, FIG. 12 and FIG. 13, respectively), to meet a patient 12 or user's feedback needs, facilitating therapy 107 continuously in a variety of ways to manage an ongoing condition based on, for example, historical data on how often patient 12 takes meals according to plan or not, what the patient 12 is currently doing (via GR or PUI, for example) when a meal is not according to plan, and a patient 12 or patient's physician remedial options preference (corrective dosing, meal or activity recommendations, or combinations thereof).

In various system embodiments, the systems 10A, 10B, or 10C (shown in FIG. 4, FIG. 5, or FIG. 6, respectively) may comprise a sensor device 20 implemented in circuitry (see, for example FIG. 20) that may be in communication with the patient device 24 (see, for example, FIG. 5 and FIG. 6). In some such embodiments, the resulting input 101 (or in some example, one of several inputs 101) may comprise a blood glucose status of a patient, which may include, but are not limited to, a continuous blood glucose reading, historic or logged blood glucose readings, predicted blood glucose readings, rate of change (ROC) in blood glucose reading and/or combinations of these blood glucose statuses. In some instances, the sensor device may be leveraged to provide an input 101 comprising a predicted blood glucose reading over time (dG/dt, for example, as shown in FIG. 11). In such instances, the sensor device 20 and processing circuitry 62 therein may be utilized to complete all or portions of the dose calculation 103 and/or ROC compensation factors 103c or other compensation factors 104. In some embodiments, the sensor device 20 may comprise a traditional glucose monitor or electrode-based CGM, but in other instances the sensor device 20 may also be present in a patient device 24 or wearable device 22 and leverage sensors or transducers present therein (for example, in processing circuitry 32 or user interface 36 portions) to derive blood glucose status of a patient using various methods, including but not limited to, photoelectric methods, mechanical or piezoelectric methods, motion based methods (using, for example, on board accelerometers or other devices) and/or combinations of these.

In various system embodiments, the system 10A shown in FIG. 4 may also comprise an insulin pump 14 in communication with the one or more processors 28A . . . 28N, and an infusion set 18 coupled to the insulin pump 14 through tubing 16, wherein the insulin pump 14 is configured to provide the optimized insulin dose 107 (see FIG. 11, FIG. 12, and FIG. 13, for example) to the patient 12 using the infusion set 18. In other embodiments as shown in FIG. 6, a system 10C may further comprise an injection device 30 (such as a smart injection pen, for example) in communication with the one or more processors 28A . . . 28N, wherein the injection device 30 is configured to provide the optimized insulin dose to the patient. In some embodiments, the systems 10A, 10B, 10C shown generally in FIG. 4, FIG. 5, and FIG. 6 may be combined such that certain components of systems may be used interchangeably within a given system utilizing an overarching control method (depicted, for example in FIG. 11, FIG. 12, and FIG. 13) to enable seamless integration of all components. For example, a patient 12 utilizing a system 10A as shown generally in FIG. 4 may sometimes opt to remove and/or pause their use of insulin pump 14 in lieu of an injection device 30 for a certain time period. Both the insulin pump 14 and injection device 30 may be integrated into system 10A via communication with other components including the cloud 26, such that insulin pump inputs 101 and/or correction factors 104 received by system 10A and stored in processors 28A . . . 28N and/or cloud 26 may be shared with injection device 30 or other system 10A components to ensure continuity of methods 100A, 100B, 100C even as types of medicament dosing used by patient 12 may have changed multiple times in a given time period.

In some such embodiments as shown in FIG. 6, the injection device 30 may comprise multiple components to enable "smart" or communications functionality with the system 10C and the one or more processors 28A . . . 28N, wherein the injection device 30 is configured to provide the optimized insulin dose to the patient. For example, in some embodiments, the injection device 30 comprises a durable or reusable communications module (sometimes called a "smart cap" for example) configured for operably engaging a single-use or disposable injection pen that may be available from a pharmaceutical provider. In such embodiments, the smart cap of the injection device 30 may enable an otherwise fully disposable injection pen to be in communication with the system 10C to better provide inputs 101, correction factors 104, and or receive optimized dose 107 recommendation and/or therapy facilitations as described here. For example, the smart cap may report to patient device 24 and/or cloud 26 on dosages selected by patient 12 and injected over a period of time so as to feed the various data needed to accomplish effective dose calculation 103 steps and/or dose optimization 105 steps as described herein.

FIG. 4 is a block diagram illustrating an example system for delivering or guiding therapy dosage, in accordance with one or more examples described in this disclosure. FIG. 4 illustrates system 10A that includes patient 12, insulin pump 14, tubing 16, infusion set 18, sensor device 20, which may be a glucose sensor, wearable device 22, patient device 24, and cloud 26. Cloud 26 represents a local, wide area or global computing network including one or more processors 28A-28N ("one or more processors 28"). In some examples, the various components may determine changes to therapy based on determination of glucose level by sensor device 20, and therefore system 10A may be configured to perform glucose sensing. In some examples, system 10A may be referred to as a continuous glucose monitoring (CGM) system 10A.

Patient 12 may be diabetic (e.g., Type 1 diabetic or Type 2 diabetic), and therefore, the glucose level in patient 12 may be uncontrolled without delivery of supplemental insulin. For example, patient 12 may not produce sufficient insulin to control the glucose level or the amount of insulin that patient 12 produces may not be sufficient due to insulin resistance that patient 12 may have developed.

To receive the supplemental insulin, patient 12 may carry insulin pump 14 that couples to tubing 16 for delivery of insulin into patient 12. Infusion set 18 may connect to the skin of patient 12 and include a cannula to deliver insulin into patient 12. Sensor device 20 may be a continuous glucose monitoring (CGM) device that, together with patient device 24 and/or processors 28, for a CGM system. One example of sensor device 20 is Guardian Sensor 3™ by Medtronic MiniMed, Inc. However, other examples of systems may be used and the example techniques should not be considered limited to the Guardian™ Sensor 3. Sensor device 20 may be coupled to patient 12 to measure the glucose level in patient 12. For example, sensor device 20 may include one of more sensing components (e.g., electrodes) that can be percutaneously inserted into subcutaneous tissue to sense glucose levels and/or other physiological signals or conditions. Insulin pump 14, tubing 16, infusion set 18, and sensor device 20 may together form an insulin pump system. One example of the insulin pump system is the MINIMED™ 670 G INSULIN PUMP SYSTEM by Medtronic MiniMed, Inc. However, other examples of insulin pump systems may be used and the example techniques should not be considered limited to the MINIMED™ 670G INSULIN PUMP SYSTEM. For example, the techniques described in this disclosure may be utilized in insulin pump systems that include wireless communication capabilities. Additionally, techniques described in this disclosure may also be utilized in other health monitoring and/or blood glucose management systems that may include, but are not limited to, CGM devices in wired or wireless communication with insulin injection device 30 such as an insulin pen (including, but not limited to smart pens such as the InPen™ device from Companion Medical, Inc.), or CGMs in wireless communication with diabetes or health management applications configured to be capable of running on standalone health devices or consumer electronic devices (embodied, for example, as a patient device 24) including, but not limited to, a wearable device 22 such as a smartwatch, smartphone, or other personal computing device for delivering, optimized dose 107 or other methods for facilitating a therapy. Thus, the example techniques should not be considered limited to insulin pump systems or smart insulin pens with wireless communication capabilities, and other types of communication, such as wired communication, may be possible. In another example, insulin pump 14, tubing 16, infusion set 18, and/or sensor device 20 may be contained in the same housing, including, but not limited to single-use housings such as disposable "patch pumps" having an integrated pump and glucose monitoring system in a single or detachably singular form factor having disposable and durable portions depending on the needs of the system 10 and the individual patient 12.

Insulin pump 14 may be a relatively small device that patient 12 can place in different locations. For instance, patient 12 may clip insulin pump 14 to the waistband of pants worn by patient 12. In some examples, to be discreet, patient 12 may place insulin pump 14 in a pocket. In general, insulin pump 14 can be worn in various places and patient 12 may place insulin pump 14 in a location based on the particular clothes patient 12 is wearing.

To provide insulin, insulin pump 14 may include one or more reservoirs (e.g., two reservoirs). A reservoir may be a plastic cartridge that holds up to N units of insulin (e.g., up to 300 units of insulin) and is locked into insulin pump 14. Insulin pump 14 may be a battery powered device that is powered by replaceable and/or rechargeable batteries.

Tubing 16, sometimes called a catheter, connects on a first end to a reservoir in insulin pump 14 and connects on a second end to infusion set 18. Tubing 16 may carry the insulin from the reservoir of insulin pump 14 to patient 12. Tubing 16 may be flexible, allowing for looping or bends to minimize concern of tubing 16 becoming detached from insulin pump 14 or infusion set 18 or concern from tubing 16 breaking.

Infusion set 18 may include a thin cannula that patient 12 inserts into a layer of fat under the skin (e.g., subcutaneous connection). Infusion set 18 may rest near the stomach of patient 12. The insulin travels from the reservoir of insulin pump 14, through tubing 16, and through the cannula in infusion set 18, and into patient 12. In some examples, patient 12 may utilize an infusion set insertion device. Patient 12 may place infusion set 18 into the infusion set insertion device, and with a push of a button on the infusion set insertion device, the infusion set insertion device may insert the cannula of infusion set 18 into the layer of fat of patient 12, and infusion set 18 may rest on top of the skin of the patient with the cannula inserted into the layer of fat of patient 12.

Sensor device 20 may include a cannula that is inserted under the skin of patient 12, such as near the stomach of patient 12 or in the arm of patient 12 (e.g., subcutaneous connection). Sensor device 20 may be configured to measure, using one or more electrodes inserted under the skin and/or into tissue of the patient, the interstitial glucose level, which is the glucose found in the fluid between the cells of patient 12. Sensor device 20 may be configured to continuously or periodically sample the glucose level and rate of change (ROC) of the glucose level over time.

Figure 7:
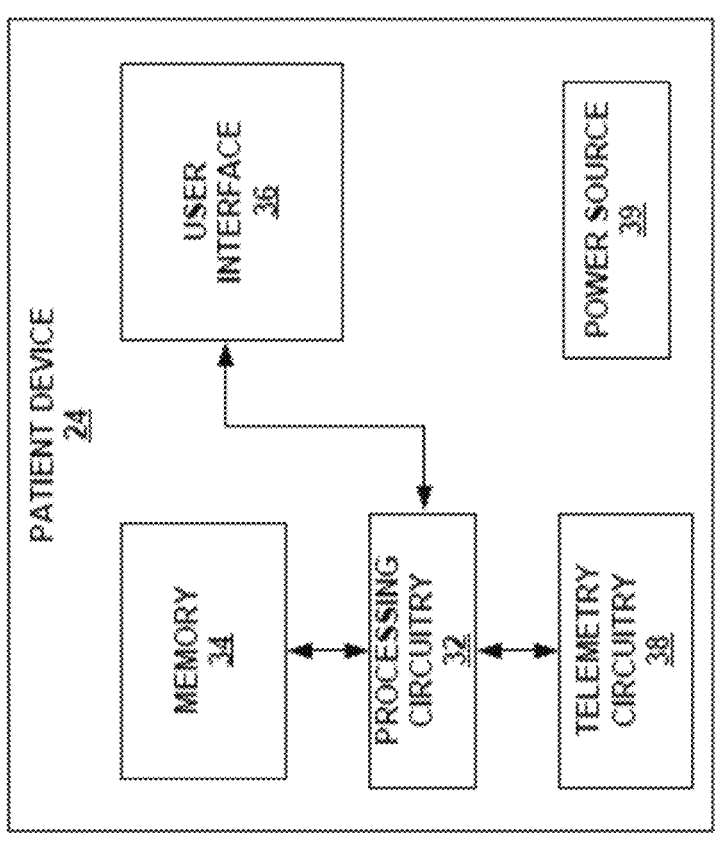
FIG. 7 is a block diagram illustrating an example of a patient device, in accordance with one or more examples described in this disclosure.

In one or more examples, insulin pump 14 and sensor device 20, and the various components illustrated in FIG. 7, may together form a closed-loop therapy delivery system. For example, patient 12 may set a target glucose level, usually measured in units of milligrams per deciliter, on insulin pump 14. Insulin pump 14 may receive the current glucose level from sensor device 20, and in response may increase or decrease the amount of insulin delivered to patient 12. For example, if the current glucose level is higher than the target glucose level, insulin pump 14 may increase the insulin. If the current glucose level is lower than the target glucose level, insulin pump 14 may temporarily cease delivery of the insulin. Insulin pump 14 may be considered as an example of an automated insulin delivery (AID) device. Other examples of AID devices may be possible, and the techniques described in this disclosure may be applicable to other AID devices.

For example, insulin pump 14 and sensor device 20 may be configured to operate together to mimic some of the ways in which a healthy pancreas works. Insulin pump 14 may be configured to deliver basal insulin, which is a small amount of insulin released continuously throughout the day. There may be times when glucose levels increase, such as due to eating or some other activity that patient 12 undertakes. Insulin pump 14 may be configured to deliver bolus insulin on demand in association with food intake or to correct an undesirably high glucose level in the bloodstream. In one or more examples, if the sensed glucose level rises above a target level, then insulin pump 14 may increase the bolus insulin to address the increase in glucose level. Insulin pump 14 may be configured to compute basal and bolus insulin delivery, and deliver the basal and bolus insulin accordingly. For instance, insulin pump 14 may determine the amount of basal insulin to deliver continuously, and then determine the amount of bolus insulin to deliver to reduce glucose level in response to an increase in glucose level due to eating or some other event.

Accordingly, in some examples, sensor device 20 may sample glucose level and rate of change in glucose level over time. Sensor device 20 may output the glucose level to insulin pump 14 (e.g., through a wireless link connection like IEEE 802.11, Wi-Fi™, Bluetooth™ or Bluetooth Low Energy (BLE)). Insulin pump 14 may compare the glucose level to a target glucose level (e.g., as set by patient 12 or clinician), and adjust the insulin dosage based on the comparison. In some examples, sensor device 20 may also output a predicted glucose level (e.g., where glucose level is expected to be in the next 30 minutes), and insulin pump 14 may adjust insulin delivery based on the predicted glucose level. The sensor device 20 may also output glucose level or other physiological parameters measurable using the impedance determinations described herein to a variety of other wired or wirelessly-connected devices to monitor and/or treat a patient's health condition. The physiological parameters could also be sent to a medical base station, or a patient device 24 as described herein to allow a patient to self-monitor and/or augment their own wellness, treatment, or disease management activities (such as consuming food or drink, exercising, or injecting medicaments (such as insulin, for example, from a separate pen injector or smart insulin pen 30 which may be used to apply dosages in lieu of, or in addition to, the insulin pump 14).

As described herein, patient 12 or a clinician may set the target glucose level on insulin pump 14; by communication with the patient 12 via application running on the patient device 24 to serve as an input 101 or correction factor 104 for the various systems and methods described herein. Patient 12 or clinician may also set target glucose levels or other glucose boundaries for a given patient by interacting with cloud 26 to ensure that processors 28A . . . 28N receive the required input 101 and/or correction factor 104 to enable the various systems and methods of the present disclosure. There may be various ways in which patient 12 or the clinician may set the target glucose level on insulin pump 14 or other devices within systems 10A, 10B, and/or 10C. As one example, patient 12 or the clinician may utilize patient device 24 to communicate with insulin pump 14. Examples of patient device 24 include, but are not limited to mobile devices, such as smartwatches, smartphones, tablet computers, laptop computers, and the like. Additionally, techniques described in this disclosure may also be utilized in other health monitoring and/or blood glucose management systems different from an insulin pump 14, including, but are not limited to, CGMs in wireless communication with insulin injection pens 30 (including, but not limited to smart pens such as the InPen™ device from Companion Medical), or CGMs in wireless communication with diabetes or health management applications configured to be capable of running on standalone health devices or patient devices 24 including, but not limited to, smartwatches, smartphones, or other personal computing devices. In some examples, patient device 24 may be a special programmer or controller for insulin pump 14, injection device 20, and/or smart cap or other multi-use components of injection device 30. Though FIG. 7 illustrates one patient device 24, in some examples, there may be a plurality of patient devices. For instance, system 10A may include a mobile device and a controller, each of which are examples of patient device 24. For ease of description only, the example techniques are described with respect to patient device 24, with the understanding that patient device 24 may be one or more patient devices.

Patient device 24 may be communicatively coupled with sensor device 20. For example, patient device 24 may be communicatively coupled with sensor device 20 via a wireless communication protocol (e.g., Wi-Fi™, IEEE 802.11, Bluetooth™, or BLE). As one example, patient device 24 may receive information from sensor device 20 through insulin pump 14, where insulin pump 14 relays the information between patient device 24 and sensor device 20. As another example, patient device 24 may receive information (e.g., glucose level or rate of change of glucose level or other physiological parameters derived from impedance measurement) directly from sensor device 20 (e.g., through a wireless link).

In one or more examples, patient device 24 may display a user interface with which patient 12 or the clinician may control insulin pump 14. For example, patient device 24 may be provided with an application or other graphical user interface for displaying a screen that allows patient 12 or the clinician to enter the target glucose level. As another example, patient device 24 may display a screen that outputs the current and/or past glucose level. In some examples, patient device 24 may output notifications to patient 12, such as notifications if the sensed glucose level is too high or too low, as well as notifications regarding any action that patient 12 needs to take. For example, if the batteries of insulin pump 14 or other medicament dispensing device, such as a smart insulin injection device 30, are low on charge, then insulin pump 14 or injection device 30 may output a low battery indication to patient device 24, and patient device 24 may in turn output a notification to patient 12 to replace or recharge the batteries.

Controlling insulin pump 14 or injection device 30 through patient device 24 is one example of a type of therapy or dose 107 provision, and should not be considered limiting. For example, insulin pump 14 may include a user interface (e.g., touch screen and/or push buttons) that allows patient 12 or the clinician to set the various glucose levels of insulin pump 14. Injection device 30 may also comprise patient 12 input interfaces for setting a recommended dose 107 output from various methods and systems described herein, including but not limited to: dose dials (incremented by various numbers or fractions of insulin units U such as 1U and/or 0.5U increments); electronic dose inputs, and/or a user interface (e.g., touch screen and/or push buttons) that allows patient 12 or the clinician to set the various glucose levels of injection device 30 based, for example on an output from the optimization steps 105 described herein, and/or directly based on a therapy facilitating or dose step 107. Also, in some examples, insulin pump 14 and/or injection device 30, or in addition to patient device 24, may each and/or both be configured to output notifications to patient 12. For instance, if the sensed glucose level is too high or too low, insulin pump 14 may output an audible or haptic output. As another example, if the battery is low, then insulin pump 14 may output a low battery indication on a display of insulin pump 14.

The above describes examples ways in which insulin pump 14 or other medicament delivery components, such as injection device 30 may deliver insulin to patient 12 based on the current glucose levels (e.g., as measured by sensor device 20). In some cases, there may be therapeutic gains by proactively delivering insulin to patient 12, rather than reacting to when glucose levels become too high or too low. See, for example systems and methods described herein using combinations of inputs 101 such as blood glucose ROC and meal (food or beverage intake) detection using GR or PUI technologies.

The glucose level in patient 12 may increase due to particular user actions. As one example, the glucose level in patient 12 may increase due to patient 12 engaging in an activity like eating or exercising. In some examples, there may be therapeutic gains if it is possible to determine that patient 12 is engaging in the activity (using for example GR, PUI, and/or leveraging functions of smart watch or other wearable device 22 or nutrition logging software such as NUTRINO™ available from Medtronic MiniMed, Inc., and optimizing 105 and facilitating therapy 107 based on the determination that patient 12 is engaging in the activity.

For example, patient 12 may forget to cause insulin pump 14 or injection device 30 to deliver insulin after eating, resulting an insulin shortfall. Alternatively, patient 12 may cause insulin pump 14 or injection device 30 to deliver insulin after eating but may have forgotten that patient 12 previously caused insulin pump 14 or injection device 30 to deliver insulin for the same meal event, resulting in an excessive insulin dosage. Also, in examples where sensor device 20 is utilized, insulin pump 14 may not take any action until after the glucose level is greater than a target level and/or the system 10A may not send notifications or instructions for a dose 107 to be injected by patient 12 using injection device 30. By proactively determining that patient 12 is engaging in an activity, insulin pump 14 and/or injection device may be able to deliver insulin and/or receive a recommended or optimized dose 107 in such a manner that the glucose level does not rise above the target level or rises only slightly above the target level (i.e., rises by less than what the glucose level would have risen if insulin were not delivered proactively). In some cases, by proactively determining that patient 12 is engaging in an activity and delivering insulin accordingly, the glucose level of patient 12 may increase more slowly.

Although the above describes proactive determination of patient 12 eating and delivering insulin accordingly, the example techniques are not so limited. The example techniques may be utilized for proactively determining an activity that patient 12 is undertaking (e.g., eating, exercising, sleeping, driving, etc.). Insulin pump 14 may then deliver insulin based on the determination of the type of activity patient 12 is undertaking.

As illustrated in FIG. 4, patient 12 may wear wearable device 22. Examples of wearable device 22 include a smartwatch or a fitness tracker, either of which may, in some examples, be configured to be worn on a patient's wrist or arm. In one or more examples, wearable device 22 includes inertial measurement unit, such as a six-axis inertial measurement unit. The six-axis inertial measurement unit may couple a 3-axis accelerometer with a 3-axis gyroscope. Accelerometers measure linear acceleration, while gyroscopes measure rotational motion. Wearable device 22 may be configured to determine one or more movement characteristics of patient 12. Examples of the one or more movement characteristics include values relating to frequency, amplitude, trajectory, position, velocity, acceleration and/or pattern of movement instantaneously or over time. The frequency of movement of the patient's arm may refer to how many times patient 12 repeated a movement within a certain time (e.g., such as frequency of movement back and forth between two positions).

Patient 12 may wear wearable device 22 on his or her wrist. However, the example techniques are not so limited. Patient 12 may wear wearable device 22 on a finger, forearm, or bicep. In general, patient 12 may wear wearable device 22 anywhere that can be used to determine gestures indicative of eating, such as movement characteristics of the arm. Wearable device 22, and/or other types of patient devices 24 (including, but not limited to smartphones, smart glasses, smartwatches, fitness tracker devices) may also be used to receive a patient input comprising a gesture recognized by a gesture recognition (GR) program or perceptual user interface (PUI) resident on an least one of the one or more processors 28 either resident in the system and/or processors or processing circuitry 32 included in the circuitry of the patient device 24 or wearable device 22, for example. The following examples illustrate certain possible operations of the GR or PUI to receive inputs 101 and/or correction factors 104, such as, for example, an indication of at least one of a type and an amount of food or beverage consumed by the patient 12 as detected by a component of the system 10A (for example, the patient device 24 or wearable device 22). In other examples, the GR or PUI to receive inputs 101 and/or correction factors 104, such as, an indication of at least one of a type and a duration of exercise performed by the patient as detected by a component of the system 10A (for example, the patient device 24 or wearable device 22). Other patient 12 activities may also be detected in order to further optimize dosing or other therapeutic responses as described further herein. One example of the GR software is part of the overall software and platforms such as the KLUE™ platform available from Klue, Inc, and Medtronic MiniMed, Inc.

In one example, the manner in which patient 12 is moving his or her arm (i.e., the movement characteristics) may refer to the direction, angle, and orientation of the movement of the arm of patient 12, including values relating to frequency, amplitude, trajectory, position, velocity, acceleration and/or pattern of movement instantaneously or over time. As an example, if patient 12 is eating, then the arm of patient 12 will be oriented in a particular way (e.g., thumb is facing towards the body of patient 12), the angle of movement of the arm will be approximately a 90-degree movement (e.g., starting from plate to mouth), and the direction of movement of the arm will be a path that follows from plate to mouth. The forward/backward, up/down, pitch, roll, yaw measurements from wearable device 22 may be indicative of the manner in which patient 12 is moving his or her arm. Also, patient 12 may have a certain frequency at which patient 12 moves his or her arm or a pattern at which patient 12 moves his or her arm that is more indicative of eating, as compared to other activities, like smoking or vaping, where patient 12 may raise his or her arm to his or her mouth.

Although the above description describes wearable device 22 as being utilized to determine whether patient 12 is eating, wearable device 22 may be configured to detect movements of the arm of patient 12 (e.g., one or more movement characteristics), and the movement characteristics may be utilized to determine an activity undertaken by patient 12. For instance, the movement characteristics detected by wearable device 22 may indicate whether patient 12 is exercising, driving, sleeping, etc. As another example, wearable device 22 may indicate posture of patient 12, which may align with a posture for exercising, driving, sleeping, eating, etc. Another term for movement characteristics may be gesture movements. Accordingly, wearable device 22 may be configured to detect gesture movements (i.e., movement characteristics of the arm of patient 12) and/or posture, where the gesture and/or posture may be part of various activities (e.g., eating, exercising, driving, sleeping, etc.).

In some examples, wearable device 22 may be configured to determine, based on the detected gestures (e.g., movement characteristics of the arm of patient 12) and/or posture, the particular activity patient 12 is undertaking. For example, wearable device 22 may be configured to determine whether patient 12 is eating, exercising, driving, sleeping, etc. In some examples, wearable device 22 may output information indicative of the movement characteristics of the arm of patient 12 and/or posture of patient 12 to patient device 24, and patient device 24 may be configured to determine the activity patient 12 is undertaking.

Wearable device 22 and/or patient device 24 may be programmed with information that wearable device 22 and/or patient device 24 utilize to determine the particular activity patient 12 is undertaking. For example, patient 12 may undertake various activities throughout the day where the movement characteristics of the arm of patient 12 may be similar to the movement characteristics of the arm of patient 12 for a particular activity, but patient 12 is not undertaking that activity. As one example, patient 12 yawning and cupping his or her mouth may have a similar movement as patient 12 eating. Patient 12 picking up groceries may have similar movement as patient 12 exercising. Also, in some examples, patient 12 may be undertaking a particular activity, but wearable device 22 and/or patient device 24 may fail to determine that patient 12 is undertaking the particular activity.

Accordingly, in one or more examples, wearable device 22 and/or patient device 24 may "learn" to determine whether patient 12 is undertaking a particular activity. However, the computing resources of wearable device 22 and patient device 24 may be insufficient to performing the learning needed to determine whether patient 12 is undertaking a particular activity. It may be possible for the computing resources of wearable device 26 and patient device 24 to be sufficient to perform the learning, but for ease of description only, the following is described with respect to one or more processors 28 in cloud 26.

As illustrated in FIG. 4, system 10A includes cloud 26 that includes one or more processors 28. For example, cloud 26 includes a plurality of network devices (e.g., servers), and the plurality of devices each include one or more processors. One or more processors 28 may be processors of the plurality of network devices, and may be located within a single one of the network devices, or may be distributed across two or more of the network devices. Cloud 26 represents a cloud infrastructure that supports one or more processors 28 on which applications or operations requested by one or more users run. For example, cloud 26 provides cloud computing for using one or more processors 28, to store, manage, and process data on the network devices, rather than by patient device 24 or wearable device 22. One or more processors 28 may share data or resources for performing computations, and may be part of computing servers, web servers, database servers, and the like. One or more processors 28 may be in network devices (e.g., servers) within a datacenter or may be distributed across multiple datacenters. In some cases, the datacenters may be in different geographical locations.

One or more processors 28, as well as other processing circuitry described herein, can include any one or more microprocessors, digital signal processors (DSPs), application specific integrated circuits (ASICs), field programmable gate arrays (FPGAs), or any other equivalent integrated or discrete logic circuitry, as well as any combinations of such components. The functions attributed one or more processors 28, as well as other processing circuitry described herein, herein may be embodied as hardware, firmware, software or any combination thereof.

One or more processors 28 may be implemented as fixed-function circuits, programmable circuits, or a combination thereof. Fixed-function circuits refer to circuits that provide particular functionality and are preset on the operations that can be performed. Programmable circuits refer to circuits that can be programmed to perform various tasks and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. One or more processors 28 may include arithmetic logic units (ALUs), elementary function units (EFUs), digital circuits, analog circuits, and/or programmable cores, formed from programmable circuits. In examples where the operations of one or more processors 28 are performed using software executed by the programmable circuits, memory (e.g., on the servers) accessible by one or more processors 28 may store the object code of the software that one or more processors 28 receive and execute.

One example way in which one or more processors 28 may be configured to determine that patient 12 is undertaking an activity and determine therapy to deliver is described in U.S. Patent Publication No. 2020/0135320 A1. In general, one or more processors 28 may first go through an initial "learning" phase, in which one or more processors 28 receive information to determine behavior patterns of patient 12. Some of this information may be provided by patient 12. For example, patient 12 may be prompted or may himself/herself enter information into patient device 24 indicating that patient 12 is undertaking a particular activity, the length of the activity, and other such information that one or more processors 28 can utilize to predict behavior of patient 12. After the initial learning phase, one or more processors 28 may still update the behavior patterns based on more recent received information but require fewer to no information from patient 12.

However, there may be other examples of contextual information for patient 12 such as sleep pattern, body temperature, stress level (e.g., based on pulse and respiration), heart rate, perfusion level, respiration rate, etc. In general, there may be various biometric sensors (e.g., to measure temperature, pulse/heart rate, breathing rate, etc.), which may be part of wearable device 22, part of device 20, and/or may be separate sensors. In some examples, the biometric sensors may be part of sensor device 20.

The contextual information for patient 12 may include conditional information. For example, patient 12 may eat every 3 hours, but the exact times of when patient 12 eats may be different. In some examples, the conditional information may be a determination of whether patient 12 has eaten and if a certain amount of time (e.g., 3 hours) has passed since patient 12 ate. In general, any information that establishes a pattern of behavior may be utilized to determine whether patient 12 is engaging in a particular activity.

While the above example techniques may be beneficial in patient 12 receiving insulin at the right time, this disclosure also describes example techniques to further proactively control delivery of insulin to patient 12. In accordance with the techniques of the disclosure, system 10A may be configured to measure an impedance of tissue of patient 12. For example, sensor device 20 may be configured to apply electrical current through tissue of patient 12 and, while applying the electrical current, measure an impedance of tissue of the patient. In some examples, sensor device 20 may be configured to apply a voltage at a tissue of patient 12 and, while applying the voltage, measure an impedance of tissue of the patient.

FIG. 5 is a block diagram illustrating another example system for delivering or guiding therapy dosage, in accordance with one or more examples described in this disclosure. FIG. 5 illustrates system 10B that is similar to system 10A of FIG. 4. However, in system 10B, patient 12 may not have insulin pump 14. Rather, patient 12 may utilize a manual injection device (e.g., an insulin pen or a syringe) to deliver insulin. For example, rather than insulin pump 14 automatically delivering insulin, patient 12 (or possible a caretaker of patient 12) may fill a syringe with insulin or set the dosage amount in an insulin pen and inject himself or herself. In this example, patient device 24 may be configured to output an indication of an amount of insulin to the patient for display.

System 10B may facilitate therapy based on various inputs 101 and/or correction factors. For example, processors 28A . . . 28N, informed by various other components of system 10B may determine an amount of insulin to provide based on a given input (such as the various types discussed herein with respect to FIG. 11, FIG. 12, and FIG. 13 and may output a notification on a display on various components of system to inject the amount (for example a determined dose 103, optimized dose 105, and/or other indication of therapy facilitation indicative of an insulin dose or other medicament dose into patient 12. In some examples, patient device 24, processors 28A . . . 28N, or sensor device 20 may determine an amount of insulin to provide based on a dose calculation 103 and/or dose optimization 105 step as described herein and may output a notification on a display to inject the amount of insulin into patient 12.

FIG. 6 is a block diagram illustrating another example system for delivering or guiding therapy dosage, in accordance with one or more examples described in this disclosure. FIG. 6 illustrates system 10C that is similar to system 10A of FIG. 4 and system 10B of FIG. 5. In system 10C, patient 12 may not have insulin pump 14. Rather, patient 12 may utilize injection device 30 to deliver insulin. For example, rather than insulin pump 14 automatically delivering insulin, patient 12 (or possible a caretaker of patient 12) may utilize injection device 30 to inject himself or herself.

Injection device 30 may be different than a syringe because injection device 30 may be a device that can communicate with patient device 24 and/or other devices in system 10C. Also, injection device 30 may include a reservoir, and based on information indicative of how much therapy dosage to deliver may be able to dose out that much insulin for delivery. For example, injection device 30 may automatically set the amount of insulin based on the information received from patient device 24. In some examples, injection device 30 may be similar to insulin pump 14, but not worn by patient 12. One example of injection device 30 is an insulin pen, sometimes embodied and equipped with electronics to render it as a smart insulin pen capable of communicating and/or interacting with other components such as the patient device 24 or system 10C. Another example of injection device 30 may be an insulin pen with a smart cap, where the smart cap can be used to set particular doses of insulin and/or communicate with other components such as the patient device 24 or system 10C.

For example, system 10C may determine an input 101 such as a sensed glucose level, or ROC that is below a glucose threshold and increase an amount of insulin injected into patient 12. In some examples, cloud 26 may receive an indication of a measured blood glucose level.

System 10C may facilitate therapy based on one or more inputs 101, correction factors 104, and resulting dose or therapy facilitation steps 107. For example, patient device 24 may determine an amount of insulin to provide based on the input 101 correction factors 104, and resulting dose or therapy facilitation steps 107, and may output an instruction to cause injection device 30 to set the amount of insulin into patient 12 and to output an indication to inject the insulin into patient 12. In some examples, patient device 24 and/or cloud 26 may determine resulting dose or therapy facilitation steps 107 based on inputs 101 or correction factors 104 received from various parts of the system 10 and processed through dose calculator steps 103 and optimization steps 105.

System 10C may facilitate therapy based on resulting dose or therapy facilitation steps 107. For example, patient device 24 may determine an amount of insulin to provide based on the resulting dose or therapy facilitation steps 107 and may output an instruction to cause injection device 30 to set the amount of insulin into patient 12 and to output an indication to inject the insulin into patient 12. For instance, patient device 24 may determine that patient 12 has a sensed glucose level that is below a glucose threshold and increase an amount of insulin injected into patient 12 directed using resulting dose or therapy facilitation steps 107 if detected inputs 101 are outside of a range of threshold values.

The above examples described insulin pump 14, a syringe, and injection device 30 as example ways in which to deliver insulin. In this disclosure, the term "insulin delivery device" may generally refer to any device used to deliver insulin. Examples of insulin delivery device include insulin pump 14, a syringe, injection device 30 (including, but not limited to, a smart injection device or injection pen with a durable smart cap engaged therewith). As described, the syringe may be a device used to inject insulin but is not necessarily capable of communicating or dosing a particular amount of insulin. Injection device 30, however, may be a device used to inject insulin that may be capable of communicating with other devices (e.g., via Wi-Fi™, IEEE 802.11, Bluetooth™, or BLE) or may be capable of dosing a particular amount of insulin. Injection device 30 may be powered (e.g., battery powered), unpowered, or spring/mechanically powered device, and the syringe may be a device that requires no electrical power.

FIG. 7 is a block diagram illustrating an example of a patient device, in accordance with one or more examples described in this disclosure. While patient device 24 may generally be described as a hand-held computing device, patient device 24 may be a notebook computer, a cell phone, or a workstation, for example. In some examples, patient device 24 may be a mobile device, such as a smartphone or a tablet computer. In such examples, patient device 24 may execute an application that allows patient device 24 to perform example techniques described in this disclosure. In some examples, patient device 24 may be specialized controller for communicating with insulin pump 14.

Although the examples are described with one patient device 24, in some examples, patient device 24 may be a combination of different devices (e.g., mobile device and a controller). For instance, the mobile device may provide access to one or more processors 28 of cloud 26 through Wi-Fi™ or carrier network and the controller may provide access to insulin pump 14. In such examples, the mobile device and the controller may communicate with one another through, for example, Wi-Fi™, Bluetooth™, and/or BLE. Various combinations of a mobile device and a controller together forming patient device 24 are possible and the example techniques should not be considered limited to any one particular configuration.

As illustrated in FIG. 7, patient device 24 may include a processing circuitry 32, memory 34, user interface 36, telemetry circuitry 38, and power source 39. Memory 34 may store program instructions that, when executed by processing circuitry 32, cause processing circuitry 32 to provide the functionality ascribed to patient device 24 throughout this disclosure. In some examples, processing circuitry 32 of patient device may augment, replace, or work in concert with the one or more processors 28A . . . 28N of the various systems 10.

In some examples, memory 34 of patient device 24 may store a plurality of parameters, inputs 101, and/or correction factors 104, such as amounts of insulin to deliver, target glucose level, time of delivery etc. Processing circuitry 32 (e.g., through telemetry circuitry 38) may output the parameters stored in memory 34 to insulin pump 14 or injection device 30 for delivery of insulin to patient 12. In some examples, processing circuitry 32 may execute a notification application, stored in memory 34, that outputs notifications to patient 12, such as notification to take insulin, amount of insulin, and time to take the insulin, via user interface 36. Various devices in systems 10A, 10B, 10C may also leverage memory of other components and/or the cloud 26 or processors 28A . . . 28N to perform the various methods described herein for dose calculation 103, dose optimization 105, and therapy facilitation 107.

Memory 34 may include any volatile, non-volatile, fixed, removable, magnetic, optical, or electrical media, such as RAM, ROM, hard disk, removable magnetic disk, memory cards or sticks, NVRAM, EEPROM, flash memory, distributed memory embodied in the cloud 26 and/or processors 28A . . . 28N and the like. Processing circuitry 32 can take the form one or more microprocessors, DSPs, ASICs, FPGAs, programmable logic circuitry, or the like, and the functions attributed to processing circuitry 32 herein may be embodied as hardware, firmware, software or any combination thereof.

User interface 36 may include a button or keypad, lights, a speaker for voice commands, and a display, such as a liquid crystal (LCD). In some examples the display may be a touchscreen. As discussed in this disclosure, processing circuitry 32 may present and receive information relating to therapy via user interface 36. For example, processing circuitry 32 may receive patient input via user interface 36. The patient input may be entered, for example, by pressing a button on a keypad, entering text, or selecting an icon from a touchscreen. The patient input may be information indicative of food that patient 12 eats, such as for the initial learning phase, whether patient 12 took the insulin (e.g., through the syringe or injection device 30), and other such information.

Telemetry circuitry 38 includes any suitable hardware, firmware, software or any combination thereof for communicating with another device, such as cloud 26, insulin pump 16 or injection device 30, as applicable, wearable device 22, and sensor device 20. Telemetry circuitry 38 may receive communication with the aid of an antenna, which may be internal and/or external to patient device 24. Telemetry circuitry 38 may be configured to communicate with another computing device via wireless communication techniques, or direct communication through a wired connection. Examples of local wireless communication techniques that may be employed to facilitate communication between patient device 24 and another computing device include RF communication according to, for example, Wi-Fi™, IEEE 802.11, Bluetooth™, or BLE specification sets, infrared communication, e.g., according to an IrDA standard, or other standard or proprietary telemetry protocols. Telemetry circuitry 38 may also provide connection with carrier network for access to cloud 26. In this manner, other devices may be capable of communicating with patient device 24.

Power source 39 delivers operating power to the components of patient device 24. In some examples, power source 39 may include a battery, such as a rechargeable or non-rechargeable battery. A non-rechargeable battery may be selected to last for several years, while a rechargeable battery may be inductively charged from an external device, e.g., on a daily or weekly basis. Recharging of a rechargeable battery may be accomplished by using an alternating current (AC) outlet or through proximal inductive interaction between an external charger and an inductive charging coil within patient device 24.

In operation, telemetry circuitry 38 may receive an indication of an input 101 or correction factor 104 from a sensor device (e.g., sensor device 20). In some examples, telemetry circuitry 38 may receive an indication of a blood glucose status and processing circuitry 32 may store the input 101 and respective time when input 101 was sensed with other input 101 values to generate a plurality of values and a time value when each respective input 101 value of the plurality of input 101 values was sensed in order to derive or generate, for example, a composite input 101 which may include an indication or function of blood glucose over time (dG/dt) or a rate of change (ROC) in an input value 101 or correction factor 104.

In some examples, processing circuitry 32 may determine an amount of insulin to be provided to the patient based on inputs 101 or correction factors 104 (using for example dose calculators 103 or optimization methods 105 described herein. For example, processing circuitry 32 may perform various steps for dose calculation 103 and optimization 105 (such as a "bolus adjuster") as described herein with respect to FIG. 11, FIG. 12, and FIG. 13. In some instances, processing circuitry may also complete all steps necessary to arrive at an optimal dose 107 or otherwise facilitate therapy 107 based on a multiple inputs (such as predictive input from a GR, combined with ROC inputs received from a sensor device 20).

Figure 8:
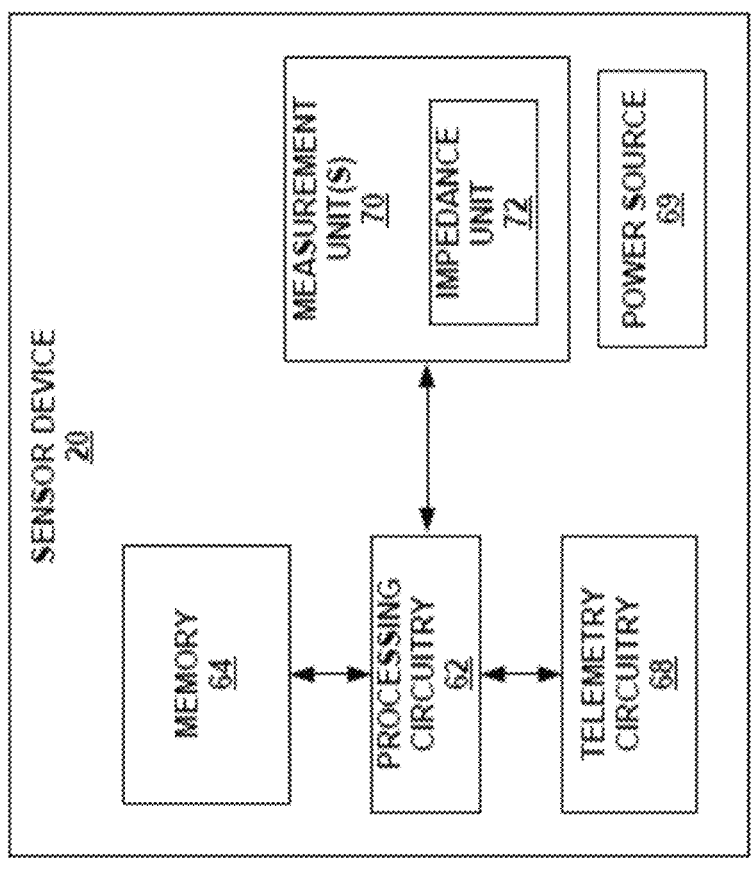
FIG. 8 is a block diagram illustrating an example of a glucose sensing device, in accordance with one or more examples described in this disclosure.

FIG. 8 is a block diagram illustrating an example of sensor device 20, in accordance with one or more examples described in this disclosure. As illustrated, device 20 includes processing circuitry 62, memory 64, telemetry circuitry 68, power source 69, and one or more sensor units 70 (also referred to herein as simply "sensor units 70"). Processing circuitry 62, memory 64, telemetry circuitry 68, and power source 69 may be similar to processing circuitry 32, memory 34, telemetry circuitry 38, and power source 39 of FIG. 6, respectively. One example of sensor device 20 is Guardian Sensor 3™ by Medtronic MiniMed, Inc. However, other examples of systems may be used and the example techniques described herein should not be considered limited to the Guardian™ Sensor 3. For example, methods and systems described herein may be primarily implemented in cloud-based 26 processors 28A . . . 28N and/or in applications housed on a patient device 24 such that inputs 101 and correction factors 104 may be derived from various types of blood glucose, sensor glucose, and other electrochemical measurements measured by sensor devices from many different manufacturers. In some embodiments, certain inputs 101 and/or correction factors 104, such as a blood glucose (BG) level may be derived from processes and/or devices such as "finger stick" glucose meters that read blood glucose levels from blood samples taken directly by the patient 12.

In embodiments using sensor devices 20, sensor units 70 may be configured to perform measurements of one or more physiological signals, levels or conditions a patient 12, including but not limited to blood glucose BG, sensor glucose SG, SG rate of change (SG ROC) or other measurements. For example, sensor device 20 may comprise a continuous glucose monitor (CGM) suitable for measuring a sensor glucose (SG) level of a patient 12 in real or near-real time as an input 101 for the various systems and methods described herein.

In addition, sensor units 70 may include impedance unit 72. Impedance unit 72 may be configured to measure an impedance of tissue of a patient. For example, impedance unit 72 may include a current source electrically coupled to a working electrode and a counter electrode to provide current through tissue of a patient. Again, the working electrode and a counter electrode may be configured to facilitate sensing a glucose level in patient 12. While providing the electrical current through the tissue, a voltage sensor of impedance unit 72 may detect a voltage at the tissue. For example, the voltage sensor of impedance unit 72 may detect a voltage between the working electrode and counter electrode (e.g., using 2 electrodes), between the working electrode and a reference electrode (e.g., using 3 electrodes), or between a sense working electrode and the reference electrode (e.g., using 4 electrodes). As used herein, a sense working electrode and a reference electrode may be used to transmit measurement current and not to transmit a working current. In contrast, the working electrode and counter electrode may be used to transmit the working current.

While the above example describes a constant current output, in some examples, sensor units 70 may be configured to apply a constant voltage output. For example, impedance unit 72 may be configured to measure an impedance of tissue of a patient while applying a voltage across the tissue. For example, impedance unit 72 may include a voltage source electrically coupled to a working electrode and a counter electrode to provide voltage across a tissue of a patient. Again, the working electrode and a counter electrode may be configured to facilitate sensing a glucose level in patient 12. While providing the electrical voltage through the tissue, a current sensor of impedance unit 72 may detect a current at the tissue. For example, the current sensor of impedance unit 72 may detect a voltage between the working electrode and counter electrode (e.g., using 2 electrodes), between the working electrode and a reference electrode (e.g., using 3 electrodes), or between a sense working electrode and the reference electrode (e.g., using 4 electrodes).

Telemetry circuitry 68 may output measurements of the patients. For example, telemetry circuitry 68 may output an indication of the impedance of tissue of the patient to one or more of insulin pump 14, patient device 24, wearable device 22, or processor(s) 28 in cloud 26. In some examples, processing circuitry 62 may determine a sensor glucose level based on sensing levels of glucose or other factors in patient's interstitial fluid. Processing circuitry 62 may determine an amount of insulin to be provided to the patient based on a dose calculation 103 and/or dose optimization 105, or processing circuitry may provide SG, SG ROC or other inputs 101 or correction factors 104 to processors 28A . . . 28N in order to populate inputs 101 and/or correction factors 104 with appropriate values to inform the methods described generally with respect to FIG. 11, FIG. 12 and FIG. 13.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

As shown in FIG. 4, FIG. 5, and FIG. 6, each of the various components of the systems 10A, 10B, and 10C may be in communication with one or more (in some embodiments all) of the other components and/or the cloud 26 to operate as described herein. Examples of local wireless communication techniques that may be employed to facilitate communication between and/or among patient device 24, sensor device 20, wearable device 22, cloud 26 (and processors 28A . . . 28N), various medicament dispensing devices (such as pump 14 and/or injection device 30), and another computing device include RF communication according to, for example, Wi-Fi™, IEEE 802.11, Bluetooth™, or BLE specification sets, infrared communication, e.g., according to an IrDA standard, or other standard or proprietary telemetry protocols. Telemetry circuitry 38 may also provide connection with carrier network for access to cloud 26. In this manner, other devices may be capable of communicating with patient device 24 and/or the cloud 26 in a direct and/or distributed manner. The cloud may advantageously house or facilitate the operation of therapy management software for creating, modifying or optimizing various inputs 101 or correction factors 104 for facilitating the therapy of a particular patient. One example of therapy management software for diabetes management is the Care-Link™ system software available from Medtronic MiniMed Inc.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including one or more processors 28 of cloud 26, one or more processors of patient device 24, one or more processors of wearable device 22, one or more processors of insulin pump 14, injection device 30, or some combination thereof. The one or more processors may be one or more integrated circuits (ICs), and/or discrete electrical circuitry, residing in various locations in the example systems described in this disclosure.

The one or more processors or processing circuitry utilized for example techniques described in this disclosure may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. The processors or processing circuitry may include arithmetic logic units (ALUs), elementary function units (EFUs), digital circuits, analog circuits, and/or programmable cores, formed from programmable circuits. In examples where the operations of the processors or processing circuitry are performed using software executed by the programmable circuits, memory accessible by the processors or processing circuitry may store the object code of the software that the processors or processing circuitry receive and execute.

Various aspects of the disclosure have been described. These and other aspects are within the scope of the following claims.

What is claimed is:

1. A system for monitoring a patient to optimize medicament dosing, the system comprising one or more processors and a patient device implemented in circuitry, the system being configured to:

receive, using the patient device, an input, the input being indicative of a blood glucose status of the patient;

determine, using the one or more processors, an initial insulin dose for the patient based on the input;

optimize, using the one or more processors, the initial insulin dose for the patient, based at least in part on a correction factor received by the one or more processors to create an optimized insulin dose for the patient, wherein the correction factor is determined based at least in part on a rate of change of a glucose level of the patient that is bounded using stored historical compensation data of the patient; and facilitate therapy, using the one or more processors, based on the optimized insulin dose.

2. The system of claim 1, wherein the input comprises a patient input to the patient device.

3. The system of claim 2, wherein the patient input comprises a gesture recognized by a gesture recognition program resident on at least one of the one or more processors and the circuitry of the patient device.

4. The system of claim 2, wherein the patient input comprises an indication of at least one of a type and an amount of food or beverage consumed by the patient.

5. The system of claim 1, wherein the input comprises a target blood glucose level for the patient.

6. The system of claim 1, further comprising a sensor device implemented in circuitry in communication with the patient device and wherein the input comprises the blood glucose status of the patient.

7. The system of claim 6, wherein the blood glucose status comprises a continuous rate of change of the glucose level of the patient as measured by the sensor device.

8. The system of claim 6, wherein the blood glucose status comprises a glucose measurement of the patient as measured by the sensor device.

9. The system of claim 1, further comprising:
   an insulin pump in communication with the one or more processors; and
   an infusion set coupled to the insulin pump through tubing, wherein the insulin pump is configured to provide the optimized insulin dose to the patient using the infusion set.

10. The system of claim 1, further comprising an injection device in communication with the one or more processors, wherein the injection device is configured to provide the optimized insulin dose to the patient.

11. A system for monitoring a patient to optimize medicament dosing, the system comprising one or more processors and a sensor device implemented in circuitry, the system being configured to:
   measure, using the sensor device, a blood glucose status of the patient;
   determine, using the one or more processors, an initial insulin dose for the patient based on the blood glucose status of the patient;
   optimize, using the one or more processors, the initial insulin dose for the patient, based at least in part on a correction factor received by the one or more processors to create an optimized insulin dose for the patient, wherein the correction factor is determined based at least in part on a rate of change of a glucose level of the patient that is bounded using stored historical compensation data of the patient; and
   facilitate therapy, using the one or more processors, based on the optimized insulin dose.

12. The system of claim 11, wherein the correction factor comprises a patient input received from a patient device in communication with the one or more processors.

13. The system of claim 12, wherein the patient input comprises an indication of at least one of a type and an amount of food or beverage consumed by the patient as detected by the patient device.

14. The system of claim 12, wherein the patient input comprises an indication of at least one of a type and a duration of exercise performed by the patient as detected by the patient device.

15. The system of claim 11, wherein the correction factor comprises a gesture recognized by a gesture recognition program resident on at least one of the one or more processors.

16. The system of claim 11, wherein the correction factor comprises a target blood glucose level for the patient.

17. The system of claim 11, wherein the blood glucose status comprises a glucose measurement of the patient as measured by the sensor device.

18. The system of claim 11, wherein the blood glucose status comprises a continuous rate of change of the glucose level of the patient as measured by the sensor device.

19. A method for monitoring a patient to optimize medicament dosing, the method comprising:
   measuring, using a sensor device implemented in circuitry, a blood glucose status of the patient;
   determining, using one or more processors, an initial insulin dose for the patient based on the blood glucose status of the patient;
   optimizing, using the one or more processors, the initial insulin dose for the patient, based at least in part on a correction factor received by the one or more processors to create an optimized insulin dose for the patient, wherein the correction factor is determined based at least in part on a rate of change of a glucose level of the patient that is bounded using stored historical compensation data of the patient; and
   facilitating therapy, using the one or more processors, based on the optimized insulin dose.

20. The method of claim 19, wherein the blood glucose status comprises a continuous rate of change of the glucose level of the patient as measured by the sensor device.

* * * * *